US011766448B2

(12) United States Patent
Wilson et al.

(10) Patent No.: US 11,766,448 B2
(45) Date of Patent: Sep. 26, 2023

(54) COMPOSITIONS AND METHODS FOR ALTERING TISSUE SPECIFICITY AND IMPROVING AAV9-MEDIATED GENE TRANSFER

(71) Applicant: The Trustees of The University of Pennsylvania, Philadelphia, PA (US)

(72) Inventors: James M. Wilson, Philadelphia, PA (US); Christie L. Bell, Boston, MA (US); Luc H. Vandenberghe, Weston, MA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 122 days.

(21) Appl. No.: 17/159,735

(22) Filed: Jan. 27, 2021

(65) Prior Publication Data

US 2021/0145857 A1 May 20, 2021

Related U.S. Application Data

(60) Continuation of application No. 16/564,537, filed on Sep. 9, 2019, now Pat. No. 10,918,658, which is a continuation of application No. 15/862,999, filed on Jan. 5, 2018, now Pat. No. 10,406,173, which is a division of application No. 13/985,630, filed as application No. PCT/US2012/025550 on Feb. 17, 2012, now Pat. No. 9,884,071.

(60) Provisional application No. 61/443,879, filed on Feb. 17, 2011.

(51) Int. Cl.
| | |
|---|---|
| *A61K 48/00* | (2006.01) |
| *A61K 35/76* | (2015.01) |
| *C12N 15/86* | (2006.01) |
| *C12N 15/861* | (2006.01) |
| *C07K 14/005* | (2006.01) |
| *A61K 31/7088* | (2006.01) |
| *A61K 31/685* | (2006.01) |
| *A61K 38/47* | (2006.01) |

(52) U.S. Cl.
CPC ........ *A61K 31/7088* (2013.01); *A61K 31/685* (2013.01); *A61K 38/47* (2013.01); *C12N 15/86* (2013.01); *C12N 2750/14043* (2013.01); *C12N 2750/14045* (2013.01); *C12N 2810/6027* (2013.01)

(58) Field of Classification Search
CPC .................... A61K 48/00; A61P 43/00; C12N 2750/14043; C12N 2750/14045; C12N 15/861
See application file for complete search history.

(56) References Cited

U.S. PATENT DOCUMENTS

| | | | |
|---|---|---|---|
| 4,497,797 | A | 2/1985 | Ebata et al. |
| 4,542,104 | A | 9/1985 | Stryer et al. |
| 4,757,006 | A | 7/1988 | Toole, Jr. et al. |
| 4,886,876 | A | 12/1989 | Zimmerman et al. |
| 5,004,803 | A | 4/1991 | Kaufman et al. |
| 5,045,455 | A | 9/1991 | Kuo et al. |
| 5,112,950 | A | 5/1992 | Meulien et al. |
| 5,149,637 | A | 9/1992 | Scandella et al. |
| 5,171,844 | A | 12/1992 | Van Ooyen et al. |
| 5,240,640 | A | 8/1993 | Siiman et al. |
| 5,248,771 | A | 9/1993 | Dougan |
| 5,248,772 | A | 9/1993 | Siiman et al. |
| 5,272,257 | A | 12/1993 | Gupta |
| 5,422,260 | A | 6/1995 | Kaufman et al. |
| 5,451,521 | A | 9/1995 | Kaufman et al. |
| 5,466,609 | A | 11/1995 | Siiman et al. |

(Continued)

FOREIGN PATENT DOCUMENTS

| | | |
|---|---|---|
| EP | 0162067 B1 | 11/1985 |
| EP | 0182448 A2 | 5/1986 |

(Continued)

OTHER PUBLICATIONS

Adachi, K. et al., A new recombinant adeno-associated virus (AAV)-based random peptide display library system: Infection-defective AAV1.9-3 as a novel detargeted platform for vector evolution, Gene Therapy and Regulation, vol. 5(1):31-55, Jan. 1, 2010.

Bell, P. et al., An optimized protocol for detection of *E. coli* β-galactosidase in lung tissue following gene transfer, Histochemistry and Cell Biology, vol. 124(1): 77-85, Jun. 10, 2005.

Bish, L.T. et al., Adeno-Associated Virus (AAV) Serotype 9 provides global cardiac gene transfer superior to AAV1, AAV6, AaV7, and AAV8 in the mouse and rat, Human Gene Therapy, vol. 19(12):1359-1368, Dec. 1, 2008.

(Continued)

*Primary Examiner* — Barry A Chestnut
(74) *Attorney, Agent, or Firm* — Howson & Howson LLP; Colleen M. Schaller

(57) ABSTRACT

A method of altering the targeting and/or cellular uptake efficiency of an adeno-associated virus (AAV) viral vector having a capsid containing an AAV9 cell surface binding domain is described. The method involves modifying a clade F cell surface receptor which comprises a glycan having a terminal sialic acid residue and a penultimate β-galactose residue. The modification may involve retargeting the vector by temporarily functionally ablate AAV9 binding in a subset of cells, thereby redirecting the vector to another subset of cells. Alternatively, the modification may involve increasing cellular update efficiency by treating the cells with a neuraminidase to expose cell surface β-galactose. Also provided are compositions containing the AAV9 vector and a neuraminidase. Also provided is a method for purifying AAV9 using β-galactose linked to solid support. Also provided are mutant vectors which have been modified to alter their targeting specificity, including mutant AAV9 in which the galactose binding domain is mutated and AAV in which an AAV9 galactose binding domain is engineered.

14 Claims, 5 Drawing Sheets

Specification includes a Sequence Listing.

(56) References Cited

U.S. PATENT DOCUMENTS

Figures 1A, 1B, 1C:
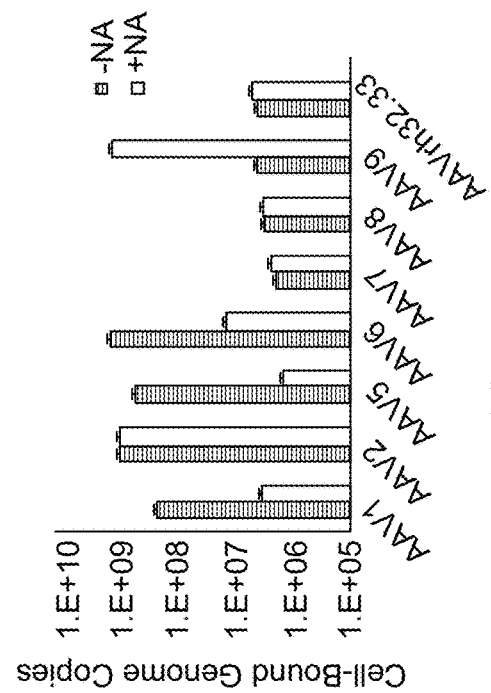

| | | | |
|---|---|---|---|
| 5,478,745 A | 12/1995 | Samulski et al. |
| 5,527,713 A | 6/1996 | Bolton et al. |
| 5,552,086 A | 9/1996 | Siiman et al. |
| 5,563,045 A | 10/1996 | Pittman et al. |
| 5,587,310 A | 12/1996 | Kane et al. |
| 5,595,886 A | 1/1997 | Chapman et al. |
| 5,633,150 A | 5/1997 | Wood et al. |
| 5,639,620 A | 6/1997 | Siiman et al. |
| 5,658,741 A | 8/1997 | Bolton et al. |
| 5,661,008 A | 8/1997 | Almstedt et al. |
| 5,681,746 A | 10/1997 | Bodner et al. |
| 5,693,499 A | 12/1997 | Yonemura et al. |
| 5,707,877 A | 1/1998 | Siiman et al. |
| 5,776,706 A | 7/1998 | Siiman et al. |
| 5,789,203 A | 8/1998 | Champan et al. |
| 5,945,293 A | 8/1999 | Siiman et al. |
| 6,074,884 A | 6/2000 | Siiman et al. |
| 6,096,273 A | 8/2000 | Kayyem et al. |
| 6,200,560 B1 | 3/2001 | Cuoto et al. |
| 6,221,349 B1 | 4/2001 | Cuoto et al. |
| 7,906,111 B2 | 3/2011 | Wilson et al. |
| 2007/0036760 A1 | 2/2007 | Wilson et al. |
| 2011/0236353 A1 | 9/2011 | Wilson et al. |
| 2012/0046349 A1 | 2/2012 | Bell et al. |

FOREIGN PATENT DOCUMENTS

| | | | |
|---|---|---|---|
| EP | 0232112 B1 | 8/1987 |
| EP | 0270618 A1 | 12/1987 |
| EP | 0160457 B1 | 1/1991 |
| EP | 0500734 B1 | 9/1992 |
| EP | 0506757 B1 | 10/1992 |
| EP | 0533862 B1 | 3/1993 |
| EP | 0670332 A2 | 9/1995 |
| EP | 0672138 B1 | 9/1995 |
| EP | 0786474 B1 | 7/1997 |
| EP | 0795021 B1 | 9/1997 |
| EP | 0874057 B1 | 10/1998 |
| JP | 2012525150 A | 10/2012 |
| JP | 2014507145 A | 3/2014 |
| WO | WO 87/007144 A1 | 12/1987 |
| WO | WO 91/007490 A1 | 5/1991 |
| WO | WO 91/009122 A1 | 6/1991 |
| WO | WO 92/016557 A1 | 10/1992 |
| WO | WO 94/011503 A2 | 5/1994 |
| WO | WO 96/021035 A2 | 7/1996 |
| WO | WO 97/003195 A1 | 1/1997 |
| WO | WO 98/010088 A1 | 3/1998 |
| WO | WO 99/0273 51 A1 | 6/1999 |
| WO | WO 99/027140 A1 | 6/1999 |
| WO | WO 00/014197 A1 | 3/2000 |
| WO | WO 10/127097 A1 | 11/2010 |
| WO | WO 12/109570 A1 | 8/2012 |
| WO | WO-2012/109214 A1 | 8/2012 |

OTHER PUBLICATIONS

Boshart, M. et al., A very strong enhancer is located upstream of an immediate early gene of human cytomegalovirus, Cell, vol. 41(2):521-530, Jun. 1985.

Carillo-Tripp, M. et al., VIPERdb2: an enhanced and web API enabled relational database for structural virology, Nucleic Acids Research, vol. 37(sup 1):D436-D442, Nov. 2008.

Davidson, B.L. et al., Recombinant adeno-associated virus type 2, 4, and 5 vectors: Transduction of variant cell types and regions in the mammalian central nervous system, Proceedings of the National Academy of Sciences of the USA, vol. 97(7):3428-3432, Mar. 28, 2000.

Donnelly, M.L. et al., The cleavage activities of aphthovirus and cardiovirus 2A proteins., Journal of General Virology, vol. 78(Pt 1): 13-21, Jan. 1997.

Duque et al., Intravenous Administration of Self-complementary AAV9 Enables Transgene Delivery to Adult Motor Neurons, Molecular Therapy, vol. 17(7):1187-1196, Jul. 2009.

Fisher, K.J., Transduction with recombinant adeno-associated virus for gene therapy is limited by leading-strand synthesis, Journal of Virology, vol. 70(1):520-532, Jan. 1996.

Foust et al., Intravascular AAV9 preferentially targets neonatal neurons and adult astrocytes, Nature Biotechnology, vol. 27(1):59-65, Dec. 21, 2008.

Fry, E.E. et al., Crystal structure of equine rhinitis A virus in complex with its sialic acid receptor, Journal of General Virology, vol. 91(8):1971-1977, Aug. 2010.

Furler S. et al., Recombinant AAV vectors containing the foot and mouth disease virus 2A sequence confer efficient bicistronic gene expression in cultured cells and rat substantia nigra neurons, Gene Therapy, vol. 8(11):864-873, Jun. 2001.

Gao, G. et al., Novel adeno-associated viruses from rhesus monkeys as vectors for human gene therapy, Proceedings of the National Academy of Sciences of the USA, vol. 99(18):11854-11859, Sep. 3, 2002.

Gao, G. et al., Adeno-associated viruses undergo substantial evolution in primates during natural infections, Proceedings of the National Academy of Sciences of the USA, vol. 100(10):6081-6086, May 13, 2003.

Gao, G et al., Clades of adeno-associated viruses are widely disseminated in human tissues, Journal of Virology, The American Society for Microbiology, vol. 78(12):6381-6388, Jun. 1, 2004.

GenBank Accession No. AY530579, accessed Nov. 20, 2014 from http://www.ncbi.nlm.nih.gov/nuccore/AY530579.

GenBank Accession No. AY530596, accessed Nov. 20, 2014 from http://www.ncbi.nlm.nih.gov/nuccore/AY530596.

GenBank Accession No. AY530597, accessed Nov. 20, 2014 from http://www.ncbi.nlm.nih.gov/nuccore/AY530597.

Gossen, M. and Bujard, H., Tight control of gene expression in mammalian cells by tetracycline-responsive promoters, Proceedings of the National Academy of Sciences of the USA, vol. 89(12):5547-5551, Jun. 15, 1992.

Gossen, M. et al., Transcriptional activation by tetracyclines in mammalian cells (1995), Science, vol. 268(5218):1766-1769, Jun. 23, 1995.

Hansal, S.A. et al., Cutting Edge: Induction of Antigen-Specific Hyporesponsiveness by Transplantation of Hemopoietic Cells Containing an MHC Class I Transgene Regulated by a Lymphocyte-Specific Promoter, Journal of Immunology, vol. 161(3):1063-1068, Aug. 1, 1998.

Harvey, D.M. and Caskey, C. T., Inducible control of gene expression: prospects for gene therapy, Current Opinion in Chemical Biology, vol. 2(4):512-518, Jul. 1998.

Inagaki, K.S. et al., Robust Systemic Transduction with AAV9 Vectors in Mice: Efficient Global Cardiac Gene Transfer Superior to That of AAV8, Molecular Therapy, vol. 14(1):45-53, Jul. 2006.

Jay, E. et al., Chemical synthesis of a biologically active gene for human immune interferon-gamma. Prospect for site-specific mutagenesis and structure-function studies, Journal of Biological Chemistry, vol. 259(10):6311-6317, May 25, 1984.

Kern, A. et al., Identification of a Heparin-Binding Motif on Adeno-Associated Virus Type 2 Capsids, Journal of Virology, vol. 77:11072-11081, Oct. 2003.

Klump, H. et al., Retroviral vector-mediated expression of HoxB4 in hematopoietic cells using a novel coexpression, Gene Therapy, vol. 8(10):811-817, May 2001.

Li, X. et al., Synthetic muscle promoters: activities exceeding naturally occurring regulatory sequences, Natural Biotechnology, vol. 17(3):241-245, Mar. 1999.

Limberis, M.B and Wilson, J.M., Adeno-associated virus serotype 9 vectors transduce murine alveolar and nasal epithelia and can be readministered, Proceedings of the National Academy of Sciences of the USA, vol. 103(35):12993-12998, Aug. 29, 2006.

Limberis, M.P. et al., Transduction efficiencies of novel AAV vectors in mouse airway epithelium in vivo and human ciliated airway epithelium in vitro, Molecular Therapy, Academic Press, San Diego, CA, vol. 17(2):294-301, Feb. 1, 2009.

Lind et al., Novel Forms of B-Domain-Deleted Recombinant Factor VIII Molecules, European Journal of Biochemistry, vol. 232(1):19-27, Aug. 1995.

(56) References Cited

OTHER PUBLICATIONS

Magari, S.R. et al., Pharmacologic control of a humanized gene therapy system implanted into nude mice, Journal of Clinical Investigation, vol. 100(11):2865-2872, Dec. 1, 1997.
Maguire, A.M. et al., Brief Report: Safety and Efficacy of Gene Transfer for Leber's Congenital Amaurosis, New England Journal of Medicine, vol. 358(21):2240-2248, May 22, 2008.
Merrifield, R.B., Solid Phase Peptide Synthesis. I. The Synthesis of a Tetrapeptide, Journal of the American Chemical Society, vol. 85(14):2149, Jul. 1, 1963.
Mitchell, R.S. et al., Retroviral DNA Integration: ASLV, HIV, and MLV Show Distinct Target Site Preferences, PLoS Biology, vol. 2(8):E234, Aug. 17, 2004.
Miyatake, S. et al., Transcriptional targeting of herpes simplex virus for cell-specific replication, Journal of Virology, vol. 71(7):5124-32, Jul. 1997.
Montfort, W. et al., The three-dimensional structure of ricin at 2.8 A, Journal of Biological Chemistry, vol. 262(11): 5398-403, Apr. 15, 1987.
Nam, H.J. et al., Structure of Adeno-Associated Virus Serotype 8, a Gene Therapy Vector, Journal of Virology, vol. 81(22):12260-12271, Nov. 15, 2007.
Ng, R. et al., Structural Characterization of the Dual Glycan Binding Adeno-Associated Virus Serotype 6, Journal of Virology, vol. 84(24):12945-57, Dec. 2010.
No, D. et al., Ecdysone-inducible gene expression in mammalian cells and transgenic mice, Proceedings of the National Academy of Sciences of the USA, vol. 93(8):3346-3351, Apr. 16, 1996.
Opie, S.R. et al., Identification of Amino Acid Residues in the Capsid Proteins of Adeno-Associated Virus Type 2 That Contribute to Heparan Sulfate Proteoglycan Binding, Journal of Virology, vol. 77(12):6995-7006, Jun. 2003.
Piccioli, P. et al., Neuroantibodies: molecular cloning of a monoclonal antibody against substance P for expression in the central nervous system, Proceedings of the National Academy of Sciences of the USA, 88(13):5611-5, Jul. 1, 1991.
Roederer, M. et al., Cy7PE and Cy7APC: Bright new probes for immunofluorescence, Cytometry Part A, vol. 24(3):191-197, Jul. 1, 1996.
Schneidman-Duhovny, D. et al., PatchDock and SymmDock: servers for rigid and symmetric docking, Nucleic Acids Research, vol. 33(2):W363-367, Apr. 2005.
Seetharaman, J. et al., X-ray Crystal Structure of the Human Galectin-3 Carbohydrate Recognition Domain at 2.1-Å Resolution, Journal of Biological Chemistry, vol. 273(21):13047-52, May 22, 1998.
Siiman, O. et al., Immunophenotyping using gold or silver nanoparticle-polystyrene bead conjugates with multiple light scatter, Cytometry, vol. 41(4):298-307, Dec. 2000.
Thompson, J.D. et al., A comprehensive comparison of multiple sequence alignments, Nucleic Acids Research, vol. 27(13):2682-2690, Jul. 1, 1999.
Vandendrieessche, T. et al., Efficacy and safety of adeno-associated viral vectors based on serotype 8 and 9 vs. lentiviral vectors for hemophilia B gene therapy, Journal of Thrombosis and Haemostasis, vol. 5(1):16-24, Jan. 2007.
Walters, R.W. et al., Binding of Adeno-associated Virus Type 5 to 2,3-Linked Sialic Acid is Required for Gene Transfer, Journal of Biological Chemistry, vol. 276(23):20610-20616, Jun. 8, 2001.
Wang, Y. et al., Positive and negative regulation of gene expression in eukaryotic cells with an inducible transcriptional regulator, Gene Therapy, 4(5):432-441, May 1997.
Wang, Y. et al., Ligand-inducible and liver-specific target gene expression in transgenic mice, Nature Biotechnology, vol. 15(3):239-243, Mar. 1997.
Wu et al., $\alpha 2,3$ and $\alpha 2,6$ N-Linked Sialic Acids Facilitate Efficient Binding and Transduction by Adeno-Associated Virus Types 1 and 6, Journal of Virology, vol. 80(18):9093-9103, Sep. 2006.
Wu, Z. et al., Adeno-associated Virus Serotypes: Vector Toolkit for Human Gene Therapy, Molecular Therapy, 14(3):316-327, Sep. 2006.
Xiao, W. et al., Gene Therapy Vectors Based on Adeno-Associated Virus Type 1, Journal of Virology, vol. 73(5):3994-4003, May 1999.
Zakhour, M. et al., The alphGal epitope of the histo-blood group antigen family is a ligand for bovine norovirus Newbury2 expected to prevent cross-species transmission, PLoS Pathogens, vol. 5(7):e1000504, Jul. 3, 2009.
Zhang, L. et al., Efficient expression of CFTR function with adeno-associated virus vectors that carry shortened CFTR genes, Proceedings of the National Academy of Sciences of the USA, 95(17):10158-63, Aug. 18, 1998.
Vandenberghe, L.H. et al., Naturally occurring singleton residues in AAV capsid impact vector performance and illustrate structural constraints, Gene Therapy, vol. 16(12):1416-1428, Sep. 3, 2009.
Gao, G. et al., New recombinant serotypes of AAV vectors, Current Gene Therapy, Bentham Science Publishers Ltd, NL, vol. 5(3):285-297, Jun. 1, 2005.
Cearley et al., Expanded Repertoire of AAV vector serotypes mediate unique patterns of transduction in mouse brain, Molecular Therapy, vol. 16(10):1710-1718, Aug. 19, 2008.
Royo et al., Specific AAV serotypes stably transduce primary hippocampal and cortical cultures with high efficiency and low toxicity, Brain Research, Elsevier, Amsterdam, NL, vol. 1190:15-22, Nov. 17, 2007.
Royo et al., Specific AAV serotypes stably transduce primary hippocampal and cortical cultures with high efficiency and low toxicity, Molecular Therapy, Academic Press, San Diego, CA, vol. 13:S347, Jan. 1, 2006.
Allocca et al., Novel adeno-associated virus serotypes efficiently transduce murine photoreceptors, Journal of Virology, The American Society for Microbiology, vol. 81(20):11372-11380, Oct. 1, 2007.
Bell, C.L. et al., The AAV9 receptor and its modification to improve in vivo lung gene transfer in mice, Journal of Clinical Investigation, vol. 121(6):2427-2435, Jun. 1, 2011.
Kaludov et al. "Adeno-associated virus serotype 4 (AAV4) and AAV5 both require sialic acid binding for hemagglutination and efficient transduction but differ in sialic acid linkage specificity." Journal of virology 75.15 (2001): 6884-6893.
Suzuki et al. "Sialidase activity of influenza A virus in an endocytic pathway enhances viral replication," Journal of virology 79.18 (2005): 11705-11715.
Bell, et al. "Identification of the galactose binding domain of the adeno-associated virus serotype 9 capsid." Journal of virology 86.13 (2012): 7326-7333. (Epub Apr. 18, 2012).
Shen et al. "Terminal N-linked galactose is the primary receptor for adeno-associated virus 9." *Journal of Biological Chemistry* 286.15 (2011): 13532-13540, and supplemental Figs. S1-S5. (Epub Feb. 17, 2011).
International Search Report and Written Opinion for corresponding International Patent Application No. PCT/US2012/025550 dated Apr. 10, 2012.
Office Action for corresponding Australian Patent Application No. 2012219380 dated May 6, 2016.
First Office Action for corresponding Japanese Patent Application No. 101280008862.8 dated Aug. 26, 2014, and Response.
Second Office Action for corresponding Chinese Application No. 101280008862.8, dated Jun. 18, 2015.
Third Office Action for corresponding Chinese Application No. 201280008862.8, dated Dec. 15, 2015.
Communication pursuant to Rules 161(1) and 162 EPC for corresponding European Application No. 12705773.5, dated Oct. 25, 2013, and Response.
Examination Report dated Sep. 15, 2015 issued on corresponding European Patent Application No. 12705773.5, and Response.
Communication pursuant to Article 94(3) EPC for corresponding European Application No. 12705773.5, dated Jul. 19, 2017.
First Office Action with translation for corresponding Japanese Patent Application No. 2013-554622 dated Feb. 24, 2016.
Second Office Action with translation for corresponding Japanese Patent Application No. 2013-554622 dated Dec. 1, 2016.

(56) References Cited

OTHER PUBLICATIONS

Office Action issued on corresponding Mexican Patent Application No. MX/a/2013/009538, dated Mar. 14, 2016.
Second Office Action with translation issued on corresponding Mexican Patent Application No. MX/a/2013/009538, dated Nov. 14, 2016.
Third Office Action with translation issued on corresponding Mexican Patent Application No. MX/a/2013/009538, dated Jun. 21, 2017.
Notice of Allowance issued on U.S. Appl. No. 13/985,630, dated Sep. 29, 2017.
Non-Final Office Action issued on U.S. Appl. No. 13/985,630, dated Apr. 5, 2017, and Response.
Final Office Action issued on U.S. Appl. No. 13/985,630, dated Nov. 23, 2016, and Response.
Non-Final Office Action issued on U.S. Appl. No. 13/985,630, dated Jan. 8, 2016, and Response.
Interview Summary filed for U.S. Appl. No. 13/985,630, summarizing interview dated Dec. 2, 2015.
Non-Final Office Action issued on U.S. Appl. No. 13/985,630, dated Jul. 6, 2015.
Notice of Allowance issued on U.S. Appl. No. 15/862,999, dated May 1, 2019.
Non-Final Office Action issued on U.S. Appl. No. 15/862,999, dated Nov. 14, 2018, and Response.
Official Action dated Nov. 5, 2019 issued in Canadian Patent Application No. 2,826,316, and Response.
Official Action dated Oct. 2, 2018 issued in Canadian Patent Application No. 2,826,316, and Response.
Official Action dated Dec. 15, 2017 issued in Canadian Patent Application No. 2,826,316, and Response.

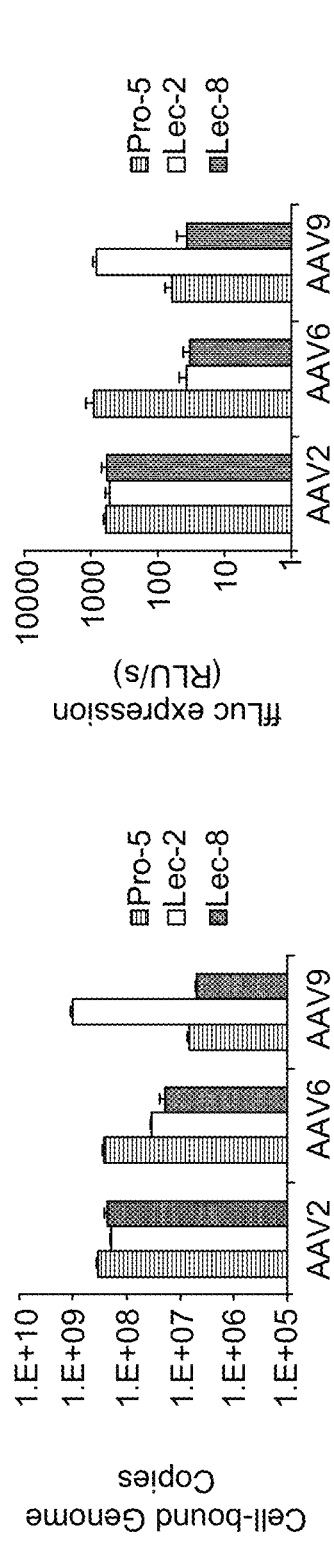
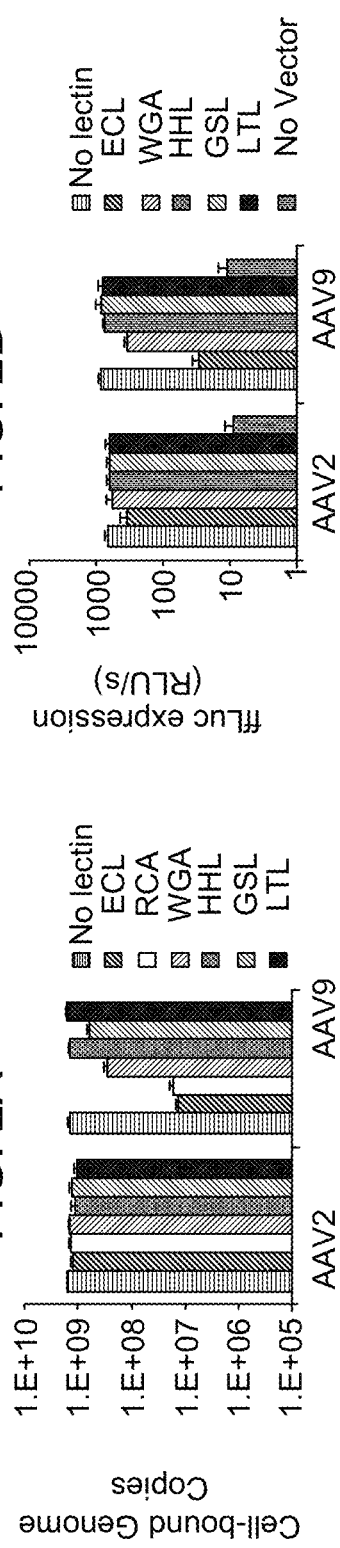
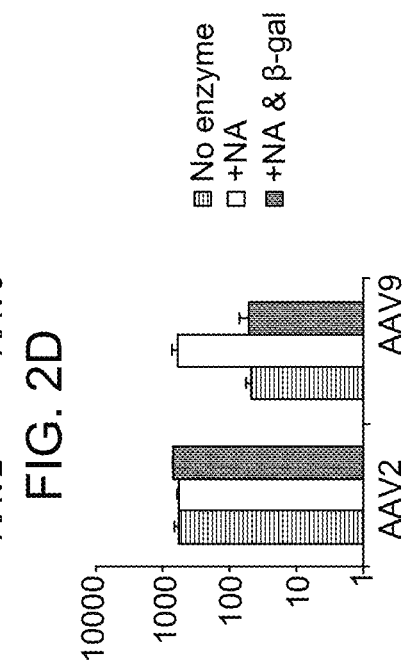
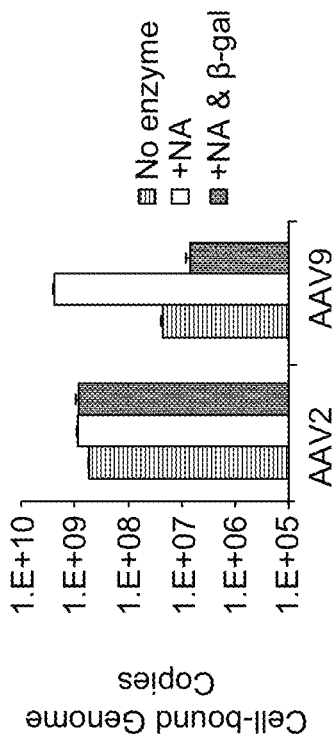

COMPOSITIONS AND METHODS FOR ALTERING TISSUE SPECIFICITY AND IMPROVING AAV9-MEDIATED GENE TRANSFER

CROSS-REFERENCE TO RELATED APPLICATIONS

This application is a continuation of U.S. patent application Ser. No. 16/564,537, filed Sep. 9, 2019, which is a continuation of U.S. patent application Ser. No. 15/862,999, filed Jan. 5, 2018, now U.S. Pat. No. 10,406,173, issued Sep. 10, 2019, which is a division of U.S. patent application Ser. No. 13/985,630, filed Aug. 15, 2013, now U.S. Pat. No. 9,884,071, issued Feb. 6, 2018, which is a national stage of International Patent Application No. PCT/US2012/025550, filed Feb. 17, 2012, now expired, which claims the benefit of the priority of U.S. Provisional Patent Application No. 61/443,879, filed Feb. 17, 2011. Each of these applications is hereby incorporated by reference in its entirety.

STATEMENT REGARDING FEDERALLY SPONSORED RESEARCH OR DEVELOPMENT

This invention was made with government support under NHLBI P01 #P01-HL-059407 awarded by the National Institutes of Health. The government has certain rights in the invention.

BACKGROUND OF THE INVENTION

The first adeno-associated viral (AAV) vectors evaluated for gene therapy were based on serotype 2 (AAV2) and were shown to transduce a variety of somatic cells following in vivo delivery [Z. Wu, et al (2006) Mol Ther, 14:316-327]. One of the first clinical successes of gene therapy used an AAV2 vector to restore some aspects of vision following subretinal injection in patients with an inherited form of blindness [A. Kern, et al, (2003) J Virol, 77: 11072-11081; A M Maguire, et al, (2008) N Engl J Med, 358: 2240-2248]. Application of AAV2 vectors for the treatment of other diseases however has not been as successful due to poor transduction efficiencies and various immunologic problems such as pre-existing neutralizing antibodies and T cell activation to the capsid [Wu, et al, cited above]. AAV2 is known to utilize heparan sulfate (HS) proteoglycans as a primary receptor for cellular recognition [Kern et al, cited above]. Additional vectors were developed based on AAV capsids from other existing serotypes such as AAV1 and its close relative AAV6, both of which showed enhanced transduction of muscle and cellular binding mediated by sialyated glycoproteins [Z. Wu et al, (2006) J Virol, 80:9093-9103; W. Xiao, et al, (1999) J Virol, 73: 3994-4003]. Vectors based on AAV5 also require binding to N-linked sialic acid (SA) while showing enhanced transduction in CNS following direct injection in brain [R W Walters et al, (2001) J Biol Chem, 276: 20610-20616; B L Davidson, et al, (2000) Proc Natl Acad Sci USA, 97:3428-3432]. The potential of AAV vectors for human gene therapy was expanded through the discovery of a large and diverse family of novel capsids from latent genomes in human and non-human primate tissues. This expanded family of AAVs number over 120 genomes spanning 6 antigenic clades [G. Gao et al, (2003) Proc Natl Acad Sci USA, 100:6081-6086; G. Gao, et al, (2004) J Virol, 78: 6381-6388; G Gao et al, (2002) Proc Natl. Acad Sci USA, 99: 11854-11859]. High resolution X-ray crystal structures and lower resolution cryo-electron microscopy reconstructed images have been determined for many of the AAV capsids demonstrating a highly conserved core region with a total of 9 surface exposed hypervariable regions [H J Nam et al, (2007) J Virol, 81:12260-12271]. Evaluation of vectors based on these novel endogenous capsids has been quite promising in terms of achieving substantially higher transduction efficiencies with diminished immunological sequelae [G. Gao et al, (2002) Proc Natl Acad. Sci, cited above].

Vectors based on adeno-associated virus (AAV) serotype 9 have emerged as leading candidates for in vivo gene delivery to many organs. AAV9 has shown significant promise in targeting the heart for treatment of cardiomyopathies [L T Bish, et al, (2008) Hum Gene Ther 19: 1359-1368] and neurons for treating diseases such as spinal muscular atrophy [S. Duque, et al, (2009) Mol Ther, 17: 1187-1196; K D Foust et al, (2009) Nat Biotechnol, 27: 59-65]. AAV9 also very efficiently transduces alveolar epithelial cells of the lung without eliciting a humoral response allowing for efficient re-administration of vector [M P Limberis and J M Wilson, (2006) Proc Natl. Acad Sci. USA, 103: 12993-12998]. However, receptor(s) mediating these tropisms have yet to be defined.

What are needed are safe, efficient methods for targeted AAV-mediated delivery of transgenes within a host.

SUMMARY OF THE INVENTION

The present invention provides a pharmacologic approach for modifying the availability of the AAV9 receptor on a desired target cell and for modifying vector efficacy. This approach was permitted due to the inventors' discovery that terminal β-galactose is the primary receptor for AAV9. Further, the approach is anticipated to be applicable to other AAV containing the AAV9 β-galactose binding domain.

In one aspect, the invention provides a method of altering the targeting and/or cellular uptake efficiency of an adeno-associated virus (AAV) viral vector having a capsid from AAV9. The method comprises delivering to a subject a composition which modifies the availability of the β-galactose cell surface receptor to bind the vector.

In one aspect, the cell surface of a target cell in a host contains a glycan having a terminal sialic acid residue and a penultimate β-galactose residue which glycan is modified by the invention to expose the β-galactose residue. In one embodiment, the method comprises delivering the AAV viral vector to a subject in combination with a neuraminidase, whereby the neuraminidase cleaves the terminal sialic acid on the glycan and increases efficiency of AAV uptake by the cell by increasing the availability of the β-galactose. The subject may be pre-treated with the neuraminidase. In one embodiment, the neuraminidase is an exo-neuraminidase (i.e., it targets terminal sialic acids for cleavage, in contrast to internal sialic acids).

In another embodiment, AAV9 vectors are redirected away from a first subset of cells which have terminal β-galactose by functionally ablating an exposed cell surface terminal β-galactose residue on the first subset of cells having receptors for AAV9 (e.g., cell surface glycans which have terminal β-galactose residues) and the AAV is thereby retargeted to a second subset of cells in the subject which have terminal β-galactose and/or the number of AAV contacting the second subset of cells is increased, thereby increasing uptake by these cells. In one embodiment, the moiety which functionally ablates the first subset of cells is delivered locally to the first subset of cells. In one embodiment, a β-galactose is enzymatically removed in a first subset of cells having the AAV9 cell surface receptors, thereby reducing or eliminating AAV uptake by said subset of cells and retargeting the AAV to a second subset of cells in the subject which have AAV9 receptors (terminal β-galactose). In one embodiment, the β-galactose is enzymatically removed by delivering galactosidase to the first subset of cells in combination with the AAV9 vectors. In another embodiment, a lectin which binds terminal β-galactose residues is delivered to the subject, which blocks β-galactose by binding these residues.

In yet another aspect, the invention provides a method of increasing gene delivery of an AAV9 vector in a cell having a surface glycans with terminal sialic acid and penultimate β-galactose residues by delivering to a subject a combination comprising a neuraminadase and an AAV9 vector, said vector further comprising a minigene having AAV inverted terminal repeats and a heterologous gene operably linked to regulatory sequences which direct its expression in an host cell.

In one aspect, the composition further provides a mutant AAV9 vector in which the native ability of wild-type (wt) AAV9 to transduce conducting airway is substantially decreased or eliminated, but liver and heart transduction similar to wtAAV9 is retained. In one embodiment, the mutant AAV has an AAV9 capsid in which the native amino acid at position 470 (Asn) is replaced. In one example, the replacement is an alanine. In another embodiment, the mutant AAV has an AAV9 capsid in which the native amino acid at position 446 (Tyr) is replaced. In one example, the replacement is an alanine. In still another embodiment, the mutant AAV has an AAV9 capsid in which the native amino acid at position 271 (Asp) is replaced. In one example, the amino acid is replaced with alanine.

In another aspect, the invention provides a method of de-targeting an AAV9 vector to airway epithelium while retaining its ability to transduce liver and heart by modifying one or more of the amino acids at position 271, 446, and 470 to Alanine or another amino acid, i.e., preferably an amino acid with a small, uncharged, side chain. In another embodiment, the amino acid has a small side chain with a methyl group which does not affect the conformation of binding site.

In a further aspect, the invention provides an AAV vector having an AAV capsid engineered to contain an AAV9 galactose binding domain. In one embodiment, the engineered AAV capsid contains the Y446, N470, A472 and V472 of AAV9 and D271, N272, and W503 of AAV9 inserted in the corresponding amino acid location of the parent AAV9.

In still another embodiment, the method provides a method for isolating an adeno-associated virus (AAV) viral vector having a capsid from AAV9. This method involves (a) exposing a sample comprising the AAV viral vector having a capsid from AAV9 to contact a molecule comprising β-galactose which has been linked to a solid support, whereby the purification target having a binding site for β-galactose is selectively bound by the molecule; (b) washing the solid support to remove material from the sample which is non-specifically bound to the solid support; and (c) separating the viral vector from the solid support.

In a further embodiment, the invention provides a composition comprising a combination of (a) a neuraminidase, (b) an adeno-associated virus (AAV) vector having an AAV9 capsid, and (c) a pharmaceutically acceptable carrier. The vector further comprises a minigene having AAV inverted terminal repeats and a heterologous gene operably linked to regulatory sequences which direct its expression in a host cell.

In still a further embodiment, the invention provides a composition comprising a combination of (a) a lectin, (b) an adeno-associated virus (AAV) vector having an AAV9 capsid and (c) a pharmaceutically acceptable carrier.

These and other aspects of the invention will be readily apparent from the following detailed description of the invention.

BRIEF DESCRIPTION OF THE INVENTION

FIGS. 1A-1C provide the results of a study of AAV binding to glycans devoid of sialic acid (SA). FIG. 1A is a schematic of N and O-linked glycans for each cell type or enzyme treatment. FIG. 1B shows the results when SA was removed from the surface of Pro-5 cells by treatment with neuraminidase (NA) and vectors were applied to NA-treated and untreated cells and evaluated for binding. Empty AAV9 capsids were screened for binding to 465 different glycans based on the average relative fluorescence units (presented in RFU) and the top five glycans that bound AAV9 identified (not shown). FIG. 1C shows the structures of the top five glycans and their representative cartoons. % CV: coefficient of variation (the ratio of the standard deviation of the data to the mean) expressed as a percentage.

FIGS. 2A-2F show the results of a study of AAV9 dependence on galactose for binding and transduction of CHO cells. AAVs 2, 6, or 9 expressing ffLuc were added to either Pro-5, Lec-2 or Lec-8 cells and incubated at 4° C. for 1 hr and total DNA was isolated to determine bound genome copies by qPCR (FIG. 2A) or cells were incubated at 37° C. for 48 hrs and analyzed for ffLuc expression (FIG. 2B). AAV2 and AAV9 were applied to NA-treated Pro-5 cells in the presence of various lectins to compete for AAV binding (FIG. 2C) or transduction (FIG. 2D). RCA was not used in transduction studies because of its toxicity to the cells. AAV2 and AAV9 were added to Pro-5 cells that were treated with either NA or both NA and β-galactosidase (NA & β-gal) to assess AAV (FIG. 2E) binding and (FIG. 2F) transduction. ffLuc, firefly luciferase; RLU, relative light units.

FIGS. 3A and 3B show the results of studies of the AAV9 capsid amino acids required for galactose binding. FIG. 3A. Specific amino acids unique to AAV9 that contain charged or polar side chains were mutated to alanine (A) to identify those responsible for galactose binding. Fourteen mutant vectors were constructed and were named according to the native amino acid and its specific position followed by the new amino acid-alanine, A. The mutants were tested for binding to Pro-5, Lec-2, and Lec-8 cells, compared to AAV9. Vector was added ($5\times10^9$ GC) to each cell line and incubated at 4° C. for 1 hour. After washing, total DNA was isolated to determine bound vector GCs by quantitative PCR. N470 was determined to be necessary for AAV9 galactose binding. FIG. 3B. Subsequently, nineteen amino acids located in close proximity to N470 were mutated to alanine to examine the effect on AAV9 galactose binding. In addition, four other mutants were produced containing mutations of the nonpolar amino acids A472 or V473 to either serine or aspartic acid. The binding of these mutant vectors was then assessed as described above. D271, N272, Y446, and W503, as well as A472 and V473, were found to be important for AAV9 galactose binding. Data is shown as mean+SD.

FIGS. 4A and 4B provide the in vitro transduction efficiency of mutant vectors. The five mutants that lost the ability to bind to galactose (N470A, D271A, N272A, Y446A, and W503A), as well as two mutants that retained galactose binding (S469A and E500A) and an AAV9 control vector, all expressing ffLuc, were added to (FIG. 4A) Lec-2 or (FIG. 4B) Pro-5 cells at 109 GC/well (MOI=104) and ffLuc expression was measured 48 hours later. Data is shown as mean+SD. RLU, relative light units.

Figure 5:
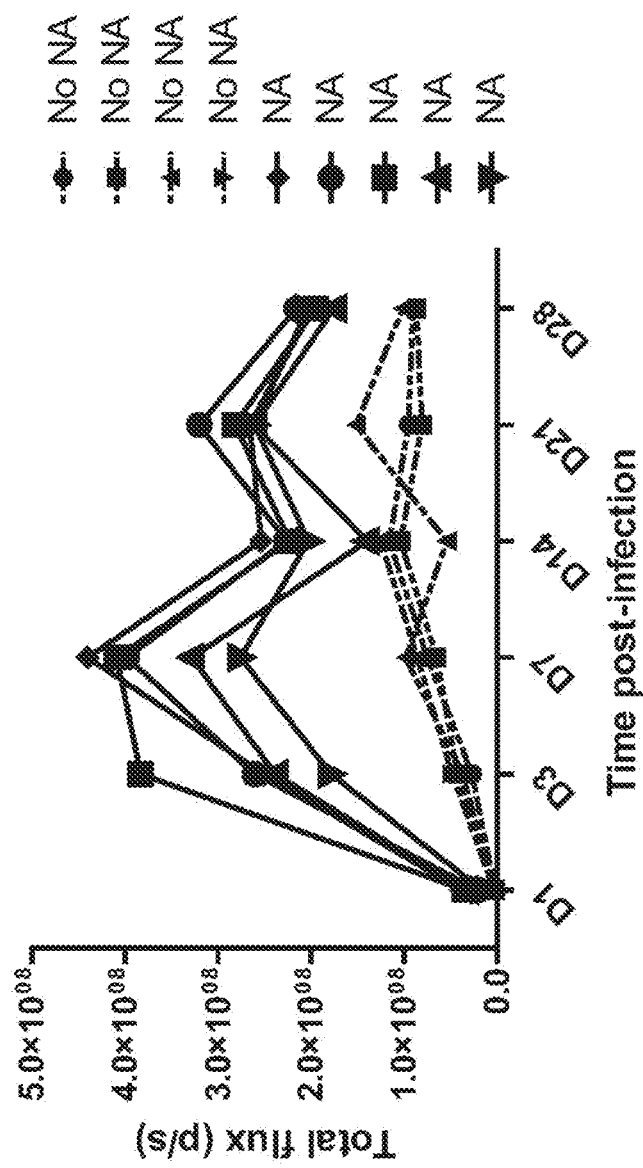

FIG. 5 is a line graph showing the results of an in vivo study of the effect of pre-treatment with neuraminidase on transgene expression in the nose after rAAV2/9 installation. Results are show as total radiant flux (photons per second (p/s)) of luciferase as imaged by luciferin intranasally at days 1, 3, 7, 14, 21 and 28 (number of days (time) post-infection).

DETAILED DESCRIPTION OF THE INVENTION

A pharmacologic approach for modifying the availability of the AAV9 receptor on a target cell and for modifying vector efficacy is described. This approach was permitted due to the inventors' discovery that terminal β-galactose is the primary receptor for AAV9. For convenience throughout this specification, reference is made to AAV9. However, it will be understood that one can substitute another AAV which contains the AAV9 capsid binding domain for cell surface terminal β-galactose or an AAV which contains another AAV capsid binding domain for the cell surface terminal β-galactose, e.g., another AAV from Clade F. Additionally, the methods and compositions described herein are useful for a vector which is a viral particle (i.e., an AAV capsid having packaged therein genomic sequences which are delivered to a host cell following uptake of the viral vector) as well as to empty AAV9 capsids (an intact AAV capsid without sequences packaged therein). Further, the invention is anticipated to be available to both wild-type and engineered capsids.

In one embodiment, AAV vector having an AAV capsid engineered to contain an AAV9 galactose binding domain, which comprises a pocket at the outside surface of the protrusions facing the 2-fold and 5-fold axes of the AAV capsid which are formed by a variable region I is provided. In one embodiment, the engineered AAV capsid contain the Y446 (conserved domain immediate before variable region (VR) IV), N470 (VR IV), A472 (VR IV) and V473 (VR IV) of AAV9 and D271 (VR I), N272 (VR I), and W503 (VR V) of AAV9 inserted in the corresponding amino acid location of the parent AAV9. While the parent AAV may have one or more of these amino acids natively, it does not natively bind galactose or contain all of these amino acids natively. For example, Y446, D271, and N272 are conserved between many serotypes; while N470 is not. Thus, a modified AAV capsid may only require engineering of the N470 (based on the position numbering of AAV9). However, such an AAV capsid may require engineering of one or more of the above amino acids in order to provide the AAV9 binding domain. In one embodiment, the engineered AAV9 is derived from an AAV which in its wild-type has sialic acid binding, but due to the engineering in of the galactose, now lacks sialic acid binding due to steric hindrance.

In another aspect, the invention provides a method of de-targeting an AAV9 vector to airway epithelium while retaining its ability to transduce liver and heart by modifying one or more of the amino acids at position 271, 446, and 470 (variable region IV) to Alanine or another amino acid. In one embodiment, the amino acid which replaces the wild-type amino acid is an amino acid with a small, uncharged, side chain. In another embodiment, the amino acid has a small side chain with a methyl group, e.g., Val, Ile, and Leu. In still another embodiment, another suitable amino acid which does not affect the conformation of the binding site in a manner which eliminates the galactose binding function is selected, e.g., Arg, His, Lys, Asp, Glu, Ser. Thr, Asp, Gln, Cys, Ala, Val, Isle, Leu, Met, Phe, Tyr, Trp. In one embodiment, the amino acid is selected from a group which excludes Pro.

Also provided are mutant AAV9 vectors which have targeting efficiencies which are different from the wt AAV9, which targets conducing airway cells, heart and liver. In one example, such a mutant AAV9 vector de-targets airway epithelium while retaining its ability to transduce liver and heart by modifying one or more of the amino acids at position 271, 446, and 470 to Alanine or another amino acid. In one embodiment, the amino acid which replaces the wild-type amino acid is an amino acid with a small, uncharged, side chain. In another embodiment, the amino acid has a small side chain with a methyl group, e.g., Val, Ile, and Leu. In still another embodiment, another suitable amino acid which does not affect the conformation of the binding site in a manner which eliminates the galactose binding function is selected, e.g., Arg, His, Lys, Asp, Glu, Ser. Thr, Asp, Gln, Cys, Ala, Val, Isle, Leu, Met, Phe, Tyr, Trp. In one embodiment, the amino acid is selected from a group which excludes Pro.

In one embodiment, the invention provides a mutant AAV9 vector in which the native ability of wild-type (wt) AAV9 to transduce conducting airway is substantially decreased or eliminated, but liver and heart transduction similar to wtAAV9 is retained. In one embodiment, the mutant AAV has an AAV9 capsid in which the native amino acid at position 470 (Asn) is replaced. In one example, the replacement is an alanine. In another embodiment, the mutant AAV has an AAV9 capsid in which the native amino acid at position 446 (Tyr) is replaced. In one example, the replacement is an alanine. In still another embodiment, the mutant AAV has an AAV9 capsid in which the native amino acid at position 271 (Asp) is replaced. In one example, the amino acid is replaced with alanine.

I. DEFINITIONS

A clade F is a group of AAV which are phylogenetically related to AAV9, hu.14/AAV9 [GenBank Accession No. AY530579], hu.31 [AY530596] and hu.32 [GenBank Accession No. AY530597] as determined using a Neighbor-Joining algorithm by a bootstrap value of at least 75% (of at least 1000 replicates) and a Poisson correction distance measurement of no more than 0.05, based on alignment of the AAV vp1 amino acid sequence. The Neighbor-Joining algorithm has been described extensively in the literature. See, e.g., M. Nei and S. Kumar, *Molecular Evolution and Phylogenetics* (Oxford University Press, New York (2000). Computer programs are available that can be used to implement this algorithm. For example, the MEGA v2.1 program implements the modified Nei-Gojobori method. Using these techniques and computer programs, and the sequence of an AAV vp1 capsid protein, one of skill in the art can readily determine whether a selected AAV is contained in one of the clades identified herein, in another clade, or is outside these clades.

The Clade F AAV may be naturally occurring AAV vp1 capsids. However, the AAV are not limited to naturally occurring AAV. The clade can encompass non-naturally occurring AAV, including, without limitation, recombinant, modified or altered, engineered, chimeric, hybrid, synthetic, artificial, etc., AAV which are phylogenetically related as determined using a Neighbor-Joining algorithm at least 75% (of at least 1000 replicates) and a Poisson correction distance measurement of no more than 0.05, based on alignment of the AAV vp1 amino acid sequence.

In another embodiment, a recombinant AAV may be from a clade other than a Clade F AAV having a capsid which has been engineered to contain the binding domain of AAV9 which binds to cell surface terminal β-galactose.

In another embodiment, an AAV used in the present invention is an AAV vector which comprises has a capsid which is at least 95% identical to the vp3 protein of AAV9 (amino acids 203 to 736 of SEQ ID NO: 1), at least 95% identical to the AAV9 vp2 (about aa 138 to 736 of SEQ ID NO: 1), and/or at least 95% identical to the full-length aav9 vp1 capsid (amino acids 1 to 736 or 2 to 736 of SEQ ID NO: 1). In another embodiment, the AAV is about 96%, about 97%, about 98%, or about 99%, to the vp1, vp2 and/or vp3 of wild-type AAV9 (SEQ ID NO:1) and contain the AAV9 cell surface binding domain for β-galactose. It will be understood by one of skill in the art that, since the vp3 domain contains the majority of the variable region, it is possible for an AAV to have 95% identity with AAV9 over the vp1 of AAV9, while having a higher identity with the vp3 of AAV9. In one embodiment, the AAV used to prepare an AAV vector has a capsid which is 100% identical to the AAV9 vp1, vp2 and/or vp3. In still another embodiment, the AAV used to prepare an AAV vector has an AAV9 capsid, with the exception that it contains one or more mutations as defined herein.

The term "substantial homology" or "substantial similarity," when referring to amino acids or fragments thereof, indicates that, when optimally aligned with appropriate amino acid insertions or deletions with another amino acid (or its complementary strand), there is amino acid sequence identity in at least about 95 to 99% of the aligned sequences. Preferably, the homology is over full-length sequence, or a protein thereof, e.g., a cap protein, a rep protein, or a fragment thereof which is at least 8 amino acids, or more desirably, at least 15 amino acids in length. Examples of suitable fragments are described herein.

By the term "highly conserved" is meant at least 80% identity, preferably at least 90% identity, and more preferably, over 97% identity. Identity is readily determined by one of skill in the art by resort to algorithms and computer programs known by those of skill in the art.

Generally, when referring to "identity", "homology", or "similarity" between two different adeno-associated viruses, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence. The terms "sequence identity" "percent sequence identity" or "percent identical" in the context of nucleic acid sequences refers to the residues in the two sequences which are the same when aligned for maximum correspondence. The length of sequence identity comparison may be over the full-length of the genome, the full-length of a gene coding sequence, or a fragment of at least about 500 to 5000 nucleotides, is desired. However, identity among smaller fragments, e.g. of at least about nine nucleotides, usually at least about 20 to 24 nucleotides, at least about 28 to 32 nucleotides, at least about 36 or more nucleotides, may also be desired. Similarly, "percent sequence identity" may be readily determined for amino acid sequences, over the full-length of a protein, or a fragment thereof. Suitably, a fragment is at least about 8 amino acids in length, and may be up to about 700 amino acids. Examples of suitable fragments are described herein.

Alignments are performed using any of a variety of publicly or commercially available Multiple Sequence Alignment Programs. Examples of such programs include, "Clustal W", "CAP Sequence Assembly", "MAP", and "MEME", which are accessible through Web Servers on the internet. Other sources for such programs are known to those of skill in the art. Alternatively, Vector NTI utilities are also used. There are also a number of algorithms known in the art that can be used to measure nucleotide sequence identity, including those contained in the programs described above. As another example, polynucleotide sequences can be compared using Fasta™, a program in GCG Version 6.1. Fasta™ provides alignments and percent sequence identity of the regions of the best overlap between the query and search sequences. For instance, percent sequence identity between nucleic acid sequences can be determined using Fasta™ with its default parameters (a word size of 6 and the NOPAM factor for the scoring matrix) as provided in GCG Version 6.1, herein incorporated by reference. Multiple sequence alignment programs are also available for amino acid sequences, e.g., the "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J D Thomson et al, (1999) Nucl. Acids. Res., "A comprehensive comparison of multiple sequence alignments", 27(13):2682-2690.

The term "serotype" is a distinction with respect to an AAV having a capsid which is serologically distinct from other AAV serotypes. Serologic distinctiveness is determined on the basis of the lack of cross-reactivity between antibodies to the AAV as compared to other AAV. Cross-reactivity is typically measured in a neutralizing antibody assay. For this assay polyclonal serum is generated against a specific AAV in a rabbit or other suitable animal model using the adeno-associated viruses. In this assay, the serum generated against a specific AAV is then tested in its ability to neutralize either the same (homologous) or a heterologous AAV. The dilution that achieves 50% neutralization is considered the neutralizing antibody titer. If for two AAVs the quotient of the heterologous titer divided by the homologous titer is lower than 16 in a reciprocal manner, those two vectors are considered as the same serotype. Conversely, if the ratio of the heterologous titer over the homologous titer is 16 or more in a reciprocal manner the two AAVs are considered distinct serotypes.

As used herein a "terminal" β-galactose is a cell surface receptor for an AAV9 having the wild-type binding site which is exposed such that it available sterically or otherwise for binding to the AAV9 galactose binding domain.

Unless otherwise specified, the term "about" when used to modify an number means a variance of ±10%.

As used throughout this specification and the claims, the terms "comprising" and "including" are inclusive of other components, elements, integers, steps and the like. Conversely, the term "consisting" and its variants are exclusive of other components, elements, integers, steps and the like.

II. TREATMENT REGIMENS

In one aspect, the invention provides a method of altering the targeting and/or cellular uptake efficiency of an adeno-associated virus (AAV) viral vector having an AAV9 capsid. The method comprises delivering to a subject a composition which modifies the availability of the β-galactose to bind an AAV9-based delivery vehicle. In one embodiment, the surface of the desired target cell contains a glycan having a terminal sialic acid residue and a penultimate β-galactose residue which glycan is modified by the invention to expose the β-galactose residue.

In one embodiment, the method comprises delivering the AAV viral vector to a subject in combination with a neuraminidase (NA), whereby the neuraminidase cleaves terminal sialic acid on the cell surface and increases efficiency of AAV uptake by the cell. The subject may be pre-treated with the neuraminidase.

By pre-treatment is meant that the treatment (e.g., neuraminidase) is delivered to the subject prior to the AAV9-mediated therapy. Typically, this involves administration of the pre-treatment prior to administration of the AAV9-mediated therapy. However, in certain embodiments, the transgene encoded by an AAV9 vector may be under the control of a regulatable promoter which is activated following pre-treatment. In such an embodiment, the AAV9 vector may be administered prior to, or substantially simultaneously with, administration of the pre-treatment, but administration of the activating agent for the constitutive promoter is subsequent to pre-treatment.

Neuraminidases, also known as sialidases, specifically target sialic acid for cleavage and may be purchased commercially, or obtained from a variety of sources. In one embodiment, the neuraminidase is an exo-neuraminidase, i.e., it specifically targets terminal sialic acids for cleavage, in contrast to internal sialic acids. In one embodiment, an exo-neuraminidase functions in hydrolysis of α-(2→3)-, α-(2→6)-, α-(2→8)-glycosidic linkages of terminal sialic acid residues. Examples of neuraminidases useful in the invention include, e.g., a bacterial neuraminidase, viral and mammalian neuraminidases. The neuraminidase (Acylneuraminyl hydrolase: EC3.2.1.18) can be from any source including, but not limited to, *Arthrobacter ureafaciens, Vibrio cholerae, Clostridium perfringens*, or from mammalian sources. In one embodiment, the neuraminidase is a bacterial neuraminidase such as neuraminadase type III from *Vibrio cholerae* (Sigma). However, other neuraminidase types may be selected. In another embodiment, a viral neuraminidase, e.g., an influenza neuraminidase may be selected. In still another embodiment, a mammalian neuraminidase may be selected from among, e.g., human, rodent, simian, or another mammalian source.

The neuraminidase can be formulated as a liquid or it can be as a solid, e.g., wherein the neuraminidase is admixed with conventional pharmaceutical excipients, including, e.g., being embedded or admixed in a biodegradable or bioerodable matrix. The matrix can be a time release matrix. These matrices are well known to those of ordinary skill in the art. The neuraminidase can be administered by injection or by sublingual route. In one embodiment, the vehicle is an aqueous solution (e.g., a saline, including buffered saline, or other suitable liquid carrier) that is contained within an inert container. In another variation, the composition is in the form of a suppository. The liquid form of the composition can be administered through standard methods, including intravenous, intramuscular, and subcutaneous routes, sublingual, or intranasal routes. In one embodiment, the carrier is 0.1% to 0.4% phenol in 0.9% sodium chloride (USP).

Neuraminidase may be administered at a dose of, e.g., about 300 U to about 5000 U of neuraminidase for, i.e., the equivalent to approximately 15 mg to 250 mg of neuraminidase per dose. Alternatively, lower doses such as in the range of about 0.0001 mg to 0.01 mg may be used. Alternatively, amounts between these two ranges, e.g., from 0.01 mg to about 250 mg may be used.

In one embodiment, the invention provides for AAV-mediated gene delivery in which the delivering to a subject an AAV9 viral vector (or a Clade F or a vector with an AAV9 cell (galactose) binding domain) and the neuraminidase substantially simultaneously. The neuraminidase may be formulated separately from the AAV vector and/or delivered via a different route, but at substantially the same time. Alternatively, the AAV viral vector is delivered to the subject in a carrier which further comprises the neuraminidase.

Although it is anticipated that a body will naturally clear an enzyme such as neuraminidase such that its effect is only temporary, in one embodiment, a neuraminidase inhibitor can be delivered in order to neutralize any lingering neuraminidase effect. Suitable neuraminidase inhibitors are known in the art and may include anti-viral drugs which are commercially available, e.g., Oseltaminivir (Tamiflu), Zanamivir (Relenza), Lanimavir (Inavir), and Peramivir. Typical dosage regimens for a systemic neuraminidase inhibitor such as oseltaminivir is about 75 mg orally, twice a day for 5 days or longer as prescribed. However, for use in the invention, a shorter dosing regimen, e.g., 1-2 days, and/or a lower or higher daily dose, may be desired. Alternatively, an inhaled neuraminidase inhibitor such as zanamivir may be desired for lung—related applications. Typically doses for this drug are 10 mg by inhalation, twice daily for 5 days or longer as prescribed. However, for use in the invention, a shorter dosing regimen, e.g., 1-2 days, and/or a lower or higher daily dose, may be desired. Alternatively, another type of neuraminidase inhibitor may be selected.

In another aspect, AAV vectors are redirected away from a first subset of cells which have clade F receptors by functionally ablating an exposed cell surface β-galactose residue on the first subset of cells having receptors for AAV9 (e.g., cell surface glycans which have terminal β-galactose residues and the AAV is thereby retargeted to a second subset of cells in the subject which have clade F receptor and/or the number of AAV contacting the second subset of cells is increased, thereby increasing uptake by these cells. In one embodiment, a β-galactose is enzymatically removed in a first subset of cells having AAV cell surface receptors, thereby reducing or eliminating AAV uptake by said subset of cells and retargeting the AAV to a second subset of cells in the subject which have AAV9 receptors.

In one embodiment, the moiety which functionally blocks the binding domain on the surface of the first subset of cells is delivered locally to the first subset of cells. Typically, this blocking effect remains relatively localized to the cells located proximal to the site of delivery. For example, local delivery can be accomplished, e.g., by inhalation, intranasal installation, injection directly into a joint or delivery directly into the eye, as well as by a variety of other methods know in the art.

A compound may be delivered to eliminate the effect of galactosidase, lectin, or other blocking moiety. For example, an anti-β-galactosidase may be delivered to the subject. For example, a compound such as GT-2558 [U.S. Pat. No. 4,497,797] or phenyl ethyl-beta-D-thiogalactopyranoside [PETG], may be utilized. Alternatively, another moiety may be delivered to accelerate clearance of the β-galactosidase or lectin. However, it is anticipated that the moiety (e.g., the galactosidase enzyme) will be readily cleared by the subject's body.

In one embodiment, the β-galactose is enzymatically removed by delivering galactosidase to the first subset of cells in combination with the AAV vectors. A variety of β-galactosidases may be used. In one embodiment, isoform 1, [GLB1, RefSeq: NM_000404; UniProt P16278, may be used. Suitable β-galactosidases are also available commercially available, e.g., from NewEngland Biolabs, Roche Applied Science, and Sigma Aldrich (from *E. Coli* sources). This enzyme may be formulated and delivered as described above for the neuraminidase. Doses of β-galactosidases in the range from about 0.0001 mg to about 250 mg per dose may be utilized, or about 0.001 mg to about 100 mg per dose. These doses may be adjusted as needed or desired. The β-galactosidase functions by cleaving galactose and significantly reducing or substantially eliminating AAV9 uptake by those cells in which the galactose was cleaved. In this manner, the AAV9 vector is redirected to other cells which retain the cell surface galactose.

In another embodiment, a lectin which binds β-galactose residues, and particularly, terminal β-galactose residues, is delivered to the subject in combination with an AAV vector as described herein. Amongst useful lectins are calcium-dependent (C-type) lectins such as human scavenger receptor C-type lectin (SRCL) and a human macrophage calcium-dependent (C-type) lectin. Other useful lectins include *Erythrina Cristagalli* lectin (ECL) and a Macrophage galactose lectin (MGL). Still other lectins may include lectin peanut agglutinin or wheat germ agglutinin. A number of these lectins have been described in the literature and/or can be obtained through commercial sources (e.g., Vectorlabs). As described herein, a lectin may be formulated in a suitable liquid carrier and may comprise in the range from 200 to 10,000 µg/ml, such as from 200 to 5000 µg/ml, for example from 200 to 3000 µg/ml, such as from 200 to 2000 µg/ml, for example from 200 to 1500 µg/ml lectin.

In yet another embodiment, an anti-terminal galactose antibody may be delivered to the subject.

Methods of preparing AAV9-based vectors and other AAV vectors as are described herein are known. See, e.g., US Published Patent Application No. 2007/0036760 (Feb. 15, 2007), which is incorporated by reference herein. The invention is not limited to the use of AAV9 or other clade F AAV amino acid sequences, but encompasses peptides and/or proteins containing the terminal β-galactose binding generated by other methods known in the art, including, e.g., by chemical synthesis, by other synthetic techniques, or by other methods. The sequences of any of the AAV capsids provided herein can be readily generated using a variety of techniques. Suitable production techniques are well known to those of skill in the art. See, e.g., Sambrook et al, Molecular Cloning: A Laboratory Manual, Cold Spring Harbor Press (Cold Spring Harbor, N.Y.). Alternatively, peptides can also be synthesized by the well-known solid phase peptide synthesis methods (Merrifield, (1962) *J. Am. Chem. Soc.,* 85:2149; Stewart and Young, Solid Phase Peptide Synthesis (Freeman, San Francisco, 1969) pp. 27-62). These and other suitable production methods are within the knowledge of those of skill in the art and are not a limitation of the present invention.

Methods of generating a recombinant adeno-associated virus (AAV) such as are described herein (e.g., an AAV having a cell binding domain for β-galactose) are known. Such a method involves culturing a host cell which contains a nucleic acid sequence encoding an AAV capsid; a functional rep gene; a minigene composed of, at a minimum, AAV inverted terminal repeats (ITRs) and a transgene; and sufficient helper functions to permit packaging of the minigene into the AAV capsid protein.

The components required to be cultured in the host cell to package an AAV minigene in an AAV capsid may be provided to the host cell in trans. Alternatively, any one or more of the required components (e.g., minigene, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contains the rep and/or cap proteins under the control of inducible promoters. Still other stable host cells may be generated by one of skill in the art.

The minigene, rep sequences, cap sequences, and helper functions required for producing the rAAV of the invention may be delivered to the packaging host cell in the form of any genetic element which transfer the sequences carried thereon. The selected genetic element may be delivered by any suitable method, including those described herein. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present invention. See, e.g., K. Fisher et al, (1993) *J. Virol.,* 70:520-532 and U.S. Pat. No. 5,478,745.

Unless otherwise specified, the AAV ITRs, and other selected AAV components described herein, may be readily selected from among any AAV. These ITRs or other AAV components may be readily isolated using techniques available to those of skill in the art from an AAV sequence. Such AAV may be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GenBank®, PubMed®, or the like.

A. The Minigene

The minigene is composed of, at a minimum, a transgene and its regulatory sequences, and 5' and 3' AAV inverted terminal repeats (ITRs). In one embodiment, the ITRs of AAV serotype 2 are used. However, ITRs from other suitable sources may be selected. It is this minigene that is packaged into a capsid protein and delivered to a selected host cell.

1. The Transgene

The transgene is a nucleic acid sequence, heterologous to the vector sequences flanking the transgene, which encodes a polypeptide, protein, or other product, of interest. The nucleic acid coding sequence is operatively linked to regulatory components in a manner which permits transgene transcription, translation, and/or expression in a host cell.

The composition of the transgene sequence will depend upon the use to which the resulting vector will be put. For example, one type of transgene sequence includes a reporter sequence, which upon expression produces a detectable signal. These coding sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. However, desirably, the transgene is a non-marker sequence encoding a product which is useful in biology and medicine, such as proteins, peptides, RNA, enzymes, dominant negative mutants, or catalytic RNAs. Desirable RNA molecules include tRNA, dsRNA, ribosomal RNA, catalytic RNAs, siRNA, small hairpin RNA, trans-splicing RNA, and antisense RNAs. One example of a useful RNA sequence is a sequence which inhibits or extinguishes expression of a targeted nucleic acid sequence in the treated subject. Typically, suitable target sequences include oncologic targets and viral diseases. See, for examples of such targets the oncologic targets and viruses identified below in the section relating to immunogens.

The transgene may be used to correct or ameliorate gene deficiencies, which may include deficiencies in which normal genes are expressed at less than normal levels or deficiencies in which the functional gene product is not expressed. Alternatively, the transgene may provide a product to a cell which is not natively expressed in the cell type or in the host. A preferred type of transgene sequence encodes a therapeutic protein or polypeptide which is expressed in a host cell. The invention further includes using multiple transgenes. In certain situations, a different transgene may be used to encode each subunit of a protein, or to encode different peptides or proteins. This is desirable when the size of the DNA encoding the protein subunit is large, e.g., for an immunoglobulin, the platelet-derived growth factor, or a dystrophin protein. In order for the cell to produce the multi-subunit protein, a cell is infected with the recombinant virus containing each of the different subunits. Alternatively, different subunits of a protein may be encoded by the same transgene. In this case, a single transgene includes the DNA encoding each of the subunits, with the DNA for each subunit separated by an internal ribozyme entry site (IRES). This is desirable when the size of the DNA encoding each of the subunits is small, e.g., the total size of the DNA encoding the subunits and the IRES is less than five kilobases. As an alternative to an IRES, the DNA may be separated by sequences encoding a 2A peptide, which self-cleaves in a post-translational event. See, e.g., M L Donnelly, et al, (January 1997) *J. Gen. Virol.,* 78(Pt 1):13-21; S. Furler, S et al, (June 2001) *Gene Ther.,* 8(11):864-873; H. Klump, et al., (May 2001) *Gene Ther.,* 8(10):811-817. This 2A peptide is significantly smaller than an IRES, making it well suited for use when space is a limiting factor. More often, when the transgene is large, consists of multi-subunits, or two transgenes are co-delivered, rAAV carrying the desired transgene(s) or subunits are co-administered to allow them to concatamerize in vivo to form a single vector genome. In such an embodiment, a first AAV may carry an expression cassette which expresses a single transgene and a second AAV may carry an expression cassette which expresses a different transgene for co-expression in the host cell. However, the selected transgene may encode any biologically active product or other product, e.g., a product desirable for study.

Suitable transgenes may be readily selected by one of skill in the art. The selection of the transgene is not considered to be a limitation of this invention.

2. Regulatory Elements

In addition to the major elements identified above for the minigene, the vector also includes conventional control elements which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, (1985) *Cell,* 41:521-530], the SV40 promoter, the dihydrofolate reductase promoter, the β-actin promoter, the phosphoglycerol kinase (PGK) promoter, and the EF1 promoter [Invitrogen]. Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied compounds, include, the zinc-inducible sheep metallothionine (MT) promoter, the dexamethasone (Dex)-inducible mouse mammary tumor virus (MMTV) promoter, the T7 polymerase promoter system [International Patent Publication No. WO 98/10088]; the ecdysone insect promoter [No et al, (1996) *Proc. Natl. Acad. Sci. USA,* 93:3346-3351], the tetracycline-repressible system [Gossen et al, (1992) *Proc. Natl. Acad. Sci. USA,* 89:5547-5551], the tetracycline-inducible system [Gossen et al, (1995) *Science,* 268:1766-1769, see also Harvey et al, (1998) *Curr. Opin. Chem. Biol.,* 2:512-518], the RU486-inducible system [Wang et al, (1997) *Nat. Biotech.,* 15:239-243 and Wang et al, (1997) *Gene Ther.,* 4:432-441] and the rapamycin-inducible system [Magari et al, (1997) *J Clin. Invest.,* 100:2865-2872]. Other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

Another embodiment of the transgene includes a gene operably linked to a tissue-specific promoter. For instance, if expression in skeletal muscle is desired, a promoter active in muscle should be used. These include the promoters from genes encoding skeletal β-actin, myosin light chain 2A, dystrophin, muscle creatine kinase, as well as synthetic muscle promoters with activities higher than naturally-occurring promoters (see Li et al., (1999) Nat. Biotech., 17:241-245). Examples of promoters that are tissue-specific are known for liver (albumin, Miyatake et al., (1997) J. Virol., 71:5124-32; hepatitis B virus core promoter, Sandig et al., (1996) Gene Ther., 3:1002-9; alpha-fetoprotein (AFP), Arbuthnot et al., (1996) Hum. Gene Ther., 7:1503-14), bone osteocalcin (Stein et al., (1997) Mol. Biol. Rep., 24:185-96); bone sialoprotein (Chen et al., (1996) J. Bone Miner. Res., 11:654-64), lymphocytes (CD2, Hansal et al., (1998) J. Immunol., 161:1063-8; immunoglobulin heavy chain; T cell receptor chain), neuronal such as neuron-specific enolase (NSE) promoter (Andersen et al., (1993) Cell. Mol. Neurobiol., 13:503-15), neurofilament light-chain gene (Piccioli et al., (1991) Proc. Natl. Acad. Sci. USA, 88:5611-5), and the neuron-specific vgf gene (Piccioli et al., (1995) Neuron, 15:373-84), among others.

The combination of the transgene, promoter/enhancer, and 5' and 3' AAV ITRs is referred to as a "minigene" for ease of reference herein. Provided with the teachings of this invention, the design of such a minigene can be made by resort to conventional techniques.

3. Delivery of the Minigene to a Packaging Host Cell

The minigene can be carried on any suitable vector, e.g., a plasmid, which is delivered to a host cell. The plasmids useful in this invention may be engineered such that they are suitable for replication and, optionally, integration in prokaryotic cells, mammalian cells, or both. These plasmids (or other vectors carrying the 5' AAV ITR-heterologous molecule-3' AAV ITR) contain sequences permitting replication of the minigene in eukaryotes and/or prokaryotes and selection markers for these systems. Selectable markers or reporter genes may include sequences encoding geneticin, hygromicin or purimycin resistance, among others. The plasmids may also contain certain selectable reporters or marker genes that can be used to signal the presence of the vector in bacterial cells, such as ampicillin resistance. Other components of the plasmid may include an origin of replication and an amplicon, such as the amplicon system employing the Epstein Barr virus nuclear antigen. This amplicon system, or other similar amplicon components permit high copy episomal replication in the cells. Preferably, the molecule carrying the minigene is transfected into the cell, where it may exist transiently. Alternatively, the minigene (carrying the 5' AAV ITR-heterologous molecule-3' ITR) may be stably integrated into the genome of the host cell, either chromosomally or as an episome. In certain embodiments, the minigene may be present in multiple copies, optionally in head-to-head, head-to-tail, or tail-to-tail concatamers. Suitable transfection techniques are known and may readily be utilized to deliver the minigene to the host cell.

Generally, when delivering the vector comprising the minigene by transfection, the vector is delivered in an amount from about 5 μg to about 100 μg DNA, about 10 μg to about 50 μg DNA to about $1 \times 10^4$ cells to about $1 \times 10^{13}$ cells, or about $1 \times 10^5$ cells. However, the relative amounts of vector DNA to host cells may be adjusted, taking into consideration such factors as the selected vector, the delivery method and the host cells selected.

B. Packaging Host Cells

In addition to the minigene, the host cell contains the sequences which drive expression of a novel AAV capsid protein of the invention (or a capsid protein comprising a fragment thereof) in the host cell and rep sequences of the same source as the source of the AAV ITRs found in the minigene, or a cross-complementing source. The packaging host cell also requires helper functions in order to package the rAAV of the invention. Such helper functions are well known in the art and will not be duplicated herein. Similarly, methods for producing suitable vectors having AAV capsids are known. [See, e.g., US Published Patent Application No. US 2007/0036760].

Thus, the invention further provides vectors generated using the nucleic acid and amino acid sequences of the novel AAV of the invention. Such vectors are useful for a variety of purposes, including for delivery of therapeutic molecules and for use in vaccine regimens. Particularly desirable for delivery of therapeutic molecules are recombinant AAV containing capsids of the novel AAV of the invention. These, or other vector constructs containing novel AAV sequences of the invention may be used in vaccine regimens, e.g., for co-delivery of a cytokine, or for delivery of the immunogen itself.

Thus, known techniques, one of skill in the art can generate a rAAV having AAV clade F capsid, an AAV9 capsid, and/or a vector having an AAV capsid which comprises an AAV9 β-galactose binding domain. In one embodiment, a full-length capsid from a single AAV, e.g., hu.14/AAV9 [SEQ ID NO: 1] can be utilized. In another embodiment, a full-length capsid may be generated which contains one or more fragments of the AAV9 capsid (e.g., a fragment comprising the AAV9 β-galactose binding domain) fused in frame with sequences from another selected AAV, or from heterologous (i.e., non-contiguous) portions of the same AAV. In still another embodiment, a vector with a mutant AAV9 capsid or an AAV engineered to contain the AAV9 galactose binding domain are assembled using similar techniques.

The above-described recombinant vectors may be delivered to host cells according to published methods. The rAAV, preferably suspended in a physiologically compatible carrier, may be administered to a human or non-human mammalian patient. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present invention.

Optionally, the compositions of the invention may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The vectors are administered in sufficient amounts to transfect the cells and to provide sufficient levels of gene transfer and expression to provide a therapeutic benefit without undue adverse effects, or with medically acceptable physiological effects, which can be determined by those skilled in the medical arts. Conventional and pharmaceutically acceptable routes of administration include, but are not limited to, direct delivery to a desired organ (e.g., the lung, heart, or brain), oral, inhalation, intranasal, intratracheal, intraarterial, intraocular, intravenous, intramuscular, subcutaneous, intradermal, and other parental routes of administration. Routes of administration may be combined, if desired.

Dosages of the viral vector will depend primarily on factors such as the condition being treated, the age, weight and health of the patient, and may thus vary among patients. For example, a therapeutically effective human dosage of the viral vector is generally in the range of from about 0.1 mL to about 100 mL of solution containing concentrations of from about $1 \times 10^9$ to $1 \times 10^{16}$ genomes virus vector. A preferred human dosage for delivery to large organs (e.g., lung, skeletal muscle, heart or lung), or the central nervous system (e.g., brain) may be about $5 \times 10^{10}$ to $5 \times 10^{13}$ AAV genomes per 1 kg, at a volume of about 1 to 100 mL. A preferred dosage for delivery to eye (e.g., retina) is about $5 \times 10^9$ to $5 \times 10^{12}$ genome copies, at a volume of about 0.1 mL to 1 mL. The dosage will be adjusted to balance the therapeutic benefit against any side effects and such dosages may vary depending upon the therapeutic application for which the recombinant vector is employed. The levels of expression of the transgene can be monitored to determine the frequency of dosage resulting in viral vectors, preferably AAV vectors containing the minigene.

As illustrated in the examples for AAV9-based vectors, transduction of cells increased when terminal SA was enzymatically removed suggesting that the most commonly observed penultimate monosaccharide to SA, galactose, mediates AAV9 transduction. This contrasts with a number of other AAV serotypes for which uptake by glycans with terminal sialic acids (SA), which is a common mode of entry. Uptake of AAV9-based vectors by terminal SA was confirmed in cells deficient of enzymes involved in glycoprotein biogenesis and lectin interference studies. Binding of AAV9 to glycans with terminal galactose was demonstrated in glycan binding assays. Relevance of this pathway for lung-directed gene transfer was demonstrated by co-instillation of AAV9 vector with neuraminidase into mouse lung which resulted in the exposure of terminal galactose on the apical surface of conducting airway epithelial cells and a substantial increase in vector-mediated transduction of these cells which are the relevant target for gene therapy for cystic fibrosis.

Examples of therapeutic products and immunogenic products for delivery by the AAV-containing vectors of the invention are provided below. These vectors may be used for a variety of regimens, as described herein. Additionally, these vectors may be delivered in combination with one or more other vectors or active ingredients in a desired regimen.

For example, suitable transgenes may include those to be preferentially targeted to the lung, including, the conducting airway epithelial cells. Such transgenes may include those useful for treating cystic fibrosis, including, e.g., cystic fibrosis transmembrane conductance regulator (CFTR) gene, including, e.g., one or more mini-CFTR genes [L. Zhang et al, (Aug. 18, 1998) Proc. Natl. Acad Sci USA, 95(17):10158-63]. Similarly, genes for treatment of other lung conditions, including, e.g., anti-inflammatory cytokines or other molecules, useful for treatment of COPD and other lung disorders may be used.

In another example, transgenes useful for treating disorders of the retina and/or the eye more generally may include be selected such as, e.g., Retinal pigment epithelium-specific 65 kDa protein (RPE65) (for treatment of Leibers congenital amaurosis (LCA), bPDE and AIPL1 pigment epithelium-derived factor (PEDF) (e.g., for treatment of macular degeneration and diabetic retinopathy), anti-angiogenic factors including, e.g, anti-Vascular Endothelial Growth Factor (VEGF) (e.g., for treatment of wet age-related macular degeneration (AMD)), as well as caller genes associated with retinitis pigmentosa and LCA, and cone-rod dystrophies.

In still another example, transgenes useful for treating disorders of a joint, e.g., rheumatoid arthritis, may be selected. Such transgenes may be, e.g., tumor necrosis factor (TNF) alpha or interleukin 1 (IL-1) blocking agents such as, e.g., anti-TNF alpha monoclonal antibodies, soluble TNF alpha receptor, type II soluble receptor of IL-1, an IL-1 receptor antagonist (IL-1Ra), anti-inflammatory cytokines (e.g., IL-4, IL-10, IL1). Such antagonists may be, e.g., an antibody or a Fab, or a functional fragment thereof, or another moiety.

Still other genes may include those useful for treatment various conditions associated with the central nervous system including, e.g., Parkinson's Disease, Alzheimer's disease, and storage disorder; therapeutic genes associated with congenital heart disease (e.g., SERCA2a, angiopoietin-1 (Ang1) and Ang2), genes associated with systemic lysosomal storage disorders; and muscle wasting disorder (e.g., dystrophin, mini-dystrophin), amongst others.

Still other useful therapeutic products encoded by the transgene may be selected for a desired indication. Such transgenes include hormones and growth and differentiation factors including, without limitation, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), platelet-derived growth factor (PDGF), insulin growth factors I and II (IGF-I and IGF-II), any one of the transforming growth factor α superfamily, including TGFα, activins, inhibins, or any of the bone morphogenic proteins (BMP) BMPs 1-15, any one of the heregluin/neuregulin/ARIA/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Other useful transgene products include proteins that regulate the immune system including, without limitation, cytokines and lymphokines such as thrombopoietin (TPO), interleukins (IL) IL-1 through IL-25 (including, e.g., IL-2, IL-4, IL-12 and IL-18), monocyte chemoattractant protein, leukemia inhibitory factor, granulocyte-macrophage colony stimulating factor, Fas ligand, tumor necrosis factors α and β, interferons α, β, and γ, stem cell factor, flk-2/flt3 ligand. Gene products produced by the immune system are also useful in the invention. These include, without limitations, immunoglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered immunoglobulins and MHC molecules. Useful gene products also include complement regulatory proteins such as complement regulatory proteins, membrane cofactor protein (MCP), decay accelerating factor (DAF), CR1, CF2 and CD59.

Still other useful gene products include any one of the receptors for the hormones, growth factors, cytokines, lymphokines, regulatory proteins and immune system proteins. The invention encompasses receptors for cholesterol regulation and/or lipid modulation, including the low density lipoprotein (LDL) receptor, high density lipoprotein (HDL) receptor, the very low density lipoprotein (VLDL) receptor, and scavenger receptors. The invention also encompasses gene products such as members of the steroid hormone receptor superfamily including glucocorticoid receptors and estrogen receptors, Vitamin D receptors and other nuclear receptors. In addition, useful gene products include transcription factors such as jun, fos, max, mad, serum response factor (SRF), AP-1, AP2, myb, MyoD and myogenin, ETS-box containing proteins, TFE3, E2F, ATF1, ATF2, ATF3, ATF4, ZF5, NFAT, CREB, HNF-4, C/EBP, SP1, CCAAT-box binding proteins, interferon regulation factor (IRF-1), Wilms tumor protein, ETS-binding protein, STAT, GATA-box binding proteins, e.g., GATA-3, and the forkhead family of winged helix proteins.

Other useful gene products include, carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin gene product [e.g., a mini- or micro-dystrophin]. Still other useful gene products include enzymes such as may be useful in enzyme replacement therapy, which is useful in a variety of conditions resulting from deficient activity of enzyme. For example, enzymes that contain mannose-6-phosphate may be utilized in therapies for lysosomal storage diseases (e.g., a suitable gene includes that encoding β-glucuronidase (GUSB)).

Still other useful gene products include those used for treatment of hemophilia, including hemophilia B (including Factor IX) and hemophilia A (including Factor VIII and its variants, such as the light chain and heavy chain of the heterodimer and the B-deleted domain; U.S. Pat. Nos. 6,200,560 and 6,221,349). The Factor VIII gene codes for 2351 amino acids and the protein has six domains, designated from the amino to the terminal carboxy terminus as A1-A2-B-A3-C1-C2 [Wood et al, (1984) Nature, 312:330; Vehar et al., (1984) Nature 312:337; and Toole et al, (1984) Nature, 342:337]. Human Factor VIII is processed within the cell to yield a heterodimer primarily comprising a heavy chain containing the A1, A2 and B domains and a light chain containing the A3, C1 and C2 domains. Both the single chain polypeptide and the heterodimer circulate in the plasma as inactive precursors, until activated by thrombin cleavage between the A2 and B domains, which releases the B domain and results in a heavy chain consisting of the A1 and A2 domains. The B domain is deleted in the activated procoagulant form of the protein. Additionally, in the native protein, two polypeptide chains ("a" and "b"), flanking the B domain, are bound to a divalent calcium cation.

In some embodiments, the minigene comprises first 57 base pairs of the Factor VIII heavy chain which encodes the 10 amino acid signal sequence, as well as the human growth hormone (hGH) polyadenylation sequence. In alternative embodiments, the minigene further comprises the A1 and A2 domains, as well as 5 amino acids from the N-terminus of the B domain, and/or 85 amino acids of the C-terminus of the B domain, as well as the A3, C1 and C2 domains. In yet other embodiments, the nucleic acids encoding Factor VIII heavy chain and light chain are provided in a single minigene separated by 42 nucleic acids coding for 14 amino acids of the B domain [U.S. Pat. No. 6,200,560].

As used herein, a therapeutically effective amount is an amount of AAV vector that produces sufficient amounts of Factor VIII to decrease the time it takes for a subject's blood to clot. Generally, severe hemophiliacs having less than 1% of normal levels of Factor VIII have a whole blood clotting time of greater than 60 minutes as compared to approximately 10 minutes for non-hemophiliacs.

The present invention is not limited to any specific Factor VIII sequence. Many natural and recombinant forms of Factor VIII have been isolated and generated. Examples of naturally occurring and recombinant forms of Factor VII can be found in the patent and scientific literature including, U.S. Pat. Nos. 5,563,045, 5,451,521, 5,422,260, 5,004,803, 4,757,006, 5,661,008, 5,789,203, 5,681,746, 5,595,886, 5,045,455, 5,668,108, 5,633,150, 5,693,499, 5,587,310, 5,171,844, 5,149,637, 5,112,950, 4,886,876; International Patent Publication Nos. WO 94/11503, WO 87/07144, WO 92/16557, WO 91/09122, WO 97/03195, WO 96/21035, and WO 91/07490; European Patent Application Nos. EP 0 672 138, EP 0 270 618, EP 0 182 448, EP 0 162 067, EP 0 786 474, EP 0 533 862, EP 0 506 757, EP 0 874 057, EP 0 795 021, EP 0 670 332, EP 0 500 734, EP 0 232 112, and EP 0 160 457; Sanberg et al., (1992) XXth Int. Congress of the World Fed. Of Hemophilia and Lind et al., (1995) *Eur. J. Biochem.,* 232:19.

Nucleic acids sequences coding for the above-described Factor VIII can be obtained using recombinant methods or by deriving the sequence from a vector known to include the same. Furthermore, the desired sequence can be isolated directly from cells and tissues containing the same, using standard techniques, such as phenol extraction and PCR of cDNA or genomic DNA [See, e.g., Sambrook et al]. Nucleotide sequences can also be produced synthetically, rather than cloned. The complete sequence can be assembled from overlapping oligonucleotides prepared by standard methods and assembled into a complete coding sequence [See, e.g., Edge, (1981) *Nature* 292:757; Nambari et al, (1984) *Science,* 223:1299; and Jay et al, (1984) *J. Biol. Chem.* 259: 6311.

Furthermore, the invention is not limited to human Factor VIII. Indeed, it is intended that the present invention encompass Factor VIII from animals other than humans, including but not limited to companion animals (e.g., canine, felines, and equines), livestock (e.g., bovines, caprines and ovines), laboratory animals, marine mammals, large cats, etc.

The AAV vectors may contain a nucleic acid coding for fragments of Factor VIII which is itself not biologically active, yet when administered into the subject improves or restores the blood clotting time. For example, as discussed above, the Factor VIII protein comprises two polypeptide chains: a heavy chain and a light chain separated by a B-domain which is cleaved during processing. As demonstrated by the present invention, co-tranducing recipient cells with the Factor VIII heavy and light chains leads to the expression of biologically active Factor VIII. Because most hemophiliacs contain a mutation or deletion in only one of the chains (e.g., heavy or light chain), it may be possible to administer only the chain defective in the patient to supply the other chain.

Other useful gene products include non-naturally occurring polypeptides, such as chimeric or hybrid polypeptides having a non-naturally occurring amino acid sequence containing insertions, deletions or amino acid substitutions. For example, single-chain engineered immunoglobulins could be useful in certain immunocompromised patients. Other types of non-naturally occurring gene sequences include antisense molecules and catalytic nucleic acids, such as ribozymes, which could be used to reduce overexpression of a target.

Reduction and/or modulation of expression of a gene is particularly desirable for treatment of hyperproliferative conditions characterized by hyperproliferating cells, as are cancers and psoriasis. Target polypeptides include those polypeptides which are produced exclusively or at higher levels in hyperproliferative cells as compared to normal cells. Target antigens include polypeptides encoded by oncogenes such as myb, myc, fyn, and the translocation gene bcr/abl, ras, src, P53, neu, trk and EGRF. In addition to oncogene products as target antigens, target polypeptides for anti-cancer treatments and protective regimens include variable regions of antibodies made by B cell lymphomas and variable regions of T cell receptors of T cell lymphomas which, in some embodiments, are also used as target antigens for autoimmune disease. Other tumor-associated polypeptides can be used as target polypeptides such as polypeptides which are found at higher levels in tumor cells including the polypeptide recognized by monoclonal antibody 17-1A and folate binding polypeptides.

Other suitable therapeutic polypeptides and proteins include those which may be useful for treating individuals suffering from autoimmune diseases and disorders by conferring a broad based protective immune response against targets that are associated with autoimmunity including cell receptors and cells which produce "self"-directed antibodies. T cell mediated autoimmune diseases include Rheumatoid arthritis (RA), multiple sclerosis (MS), Sjögren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors (TCRs) that bind to endogenous antigens and initiate the inflammatory cascade associated with autoimmune diseases.

Still other products for delivery to target cells are known to those of skill in the art.

III. METHOD OF ISOLATION AND PURIFICATION

The present invention provides a method for isolation and detection of AAV9 by using β-galactose attached to a solid support. The invention may also be readily applied to purification of another clade F AAV having a binding sites for β-galactose or to so-called "empty AAV9 capsids" (intact capsid proteins without genomic sequences packaged therein) which contain binding sites for β-galactose. For example, it will be understood that AAV vectors containing chimeric AAV capsid, e.g., those containing portions of AAV9 or other clade F capsid protein which have β-galactose binding sites, can be detected, separated and isolated according to the invention. For convenience throughout this specification, these viral vectors and other proteins which have binding sites specific for β-galactose as described herein, are termed "purification targets". As indicated previously, it will be understood that reference to AAV9 in this section is used for shorthand purposes and does not exclude other AAV capsids having a binding sites for β-galactose.

Using the methods described herein, removal of the specifically bound viruses (or "empty capsid proteins") by elution or incubation with a high salt solution efficiently recovers AAV9 of a purity which is more desirable than is achieved with $CsCl_2$ sedimentation. In addition, this technique is fast, does not require special equipment and can be easily scaled-up. The invention further provides kits useful for isolation and detection of AAV9 capsids (whether a packaged viral particle or "empty") using the methods described herein, which utilize a single step affinity column for purification and detection of viral vectors and, optionally, a visually detectable marker system.

In one embodiment, the method provides a method for isolating a purification target. This method involves exposing a sample comprising the purification target contact a molecule comprising β-galactose which has been linked to a solid support, whereby the purification target having a binding site for β-galactose is selectively bound by the molecule. Thereafter, the solid support is washed to remove material from the sample which is non-specifically bound to the solid support. The purification target may then be separated from the solid support. Optionally, the purification target separated from the solid support is concentrated for further use. In one embodiment, the solid support is loaded in an affinity chromatography column.

The invention is well suited for separation and isolation of viral vectors having capsids from a clade F AAV or an AAV having an AAV9 cell binding domain. These AAV can be separated from the materials found in the cultures in which these viruses are produced by the ability of their capsids to specifically bind β-galactose. The method of the invention is useful in a process for separation and isolation of a clade F AAV or an AAV having an AAV9 cell binding domain from helper-dependent production cultures, as adenoviruses, AAV1, and the other viral or cellular materials found in such cultures do not specifically bind β-galactose.

For use in the present invention, one or more β-galactose molecules may be bound directly or indirectly (e.g., via a suitable linker) to a solid support, as defined herein. Alternatively, β-galactose can be found in a variety of molecules, including proteinaceious, sugar, and chemical moieties, which can be bound (directly or indirectly) to a solid support. In order to efficiently bind the AAV9, other clade F, or chimeric AAV containing an AAV9 cell binding domain, such molecules contain terminal (exo) galactose. An example of a molecule containing β-galactose is a glycan having terminal β-galactose. Such molecules may be obtained from commercial sources or prepared according to a variety of natural, synthetic, recombinant or other suitable methods.

Chemical synthesis of β-galactose is known in the art, such as TBOC or FMOC protection of alpha-amino groups. (See, Coligan, et al., *Current Protocols in Immunology*, Wiley Interscience, 1991, Unit 9). Alternatively, peptides can also be synthesized by the well known solid phase peptide synthesis methods (Merrifield, *J. Am. Chem. Soc.*, 85:2149 (1962); Stewart and Young, Solid Phase Peptide Synthesis (Freeman, San Francisco, 1969) pp. 27-62). Alternatively, a chemical molecule may be utilized which contains one or more β-galactose moieties, such that the chemical molecule is attached to a solid support. In yet another alternative, a solid support for use in purification may be chemically or otherwise modified to contain one, and preferably more than one, β-galactose moieties. Such β-galactose moieties may be directly linked to the solid support, e.g., by a covalent bond or other suitable bound which withstands binding of the β-galactose to the purification target and removal of non-specifically bound materials. Alternatively, the β-galactose moieties may be indirectly linked to the solid support, e.g., by a moiety which facilitates binding of the β-galactose to the support. Such a moiety may be a protein, a chemical moiety, or another suitable linker. Suitable methods for linking a β-galactose or terminal β-galactose-containing moiety, are known in the art, and are also available from the manufacturers of solid supports.

As used herein, the term "solid support" refers to any substance, including gels, resins, beads, powders and other solids, to which β-galactose or a molecule containing a terminal β-galactose(s) can be bound so that the β-galactose molecule bound to the solid support withstands binding of the β-galactose to the purification target and removal of non-specifically bound materials. Examples of suitable solid supports include resins composed of sepharose, agarose, cross-linked agarose, mixed agarose-polyacrylamide, or polyacrylein; beads (including microbeads); silicon; glass; microcells; microcapsules; microtiter plates; and biochips. Useful supports include those described in International Patent Publication WO 99/27351, published Jun. 3, 1999; International Patent Publication WO 99/27140, published Jun. 3, 1999; U.S. Pat. No. 6,096,273; International Patent Publication WO 00/14197, published Mar. 16, 2000, among others.

A variety of microbeads are known, including the aminodextran beads described in U.S. Pat. Nos. 6,074,884; 5,945,293; and 5,658,741 Aminodextran-coated monodispersed colloidal dispersions of magnetic ferrite [U.S. Pat. No. 5,240,640]; metal [U.S. Pat. No. 5,248,772]; polystyrene [U.S. Pat. Nos. 5,466,609; 5,707,877; 5,639,620; 5,776,706], and polystyrene-metal [U.S. Pat. Nos. 5,552,086; 5,527,713] particles may also be employed as solid supports according to this invention. Another type of solid support may contain the above-described coated substrate with a layer of colloidal-sized metallic solid overlaying the aminodextran coating. Gold/silver colloid coated polystyrene-aminodextran beads, their preparation, characterization and use in analyses of subpopulations of white blood cells in whole blood have been described. See, e.g., U.S. Pat. Nos. 5,248,772; 5,552,086; 5,945,293; O. Siiman and A. Burshteyn, *J. Phys. Chem.*, 104:9795-9810 (2000); and O. Siiman et al, *Cytometry*, 41:298-307 (2000). An alternative to this coated substrate employs carboxy-functionalized polystyrene particles as the core substrate, coated with aminodextran by EDAC coupling as described in U.S. Pat. No. 5,639,620. These and other solid supports are known to those of skill in the art and are available from a variety of commercial sources, including, without limitation, Amersham Pharmacia (Uppsula, Sweden); Pierce; Biorad (Richmond, Va.), and Beckman Coulter, among others.

In one embodiment, the solid support is composed of activated sepharose. CnBr-activated sepharose may be purchased from Amersham Pharmacia. However, other sources of sepharose and activated sepharose are known, as are methods of activation and activation compounds. Examples of suitable activated sepharose include CnBr-, carbonyldiimidazole-, glutaraldehyde-, hydroxysuccinimide-, and tosyl chloride-activated sepharose.

Methods for binding the β-galactose, or the molecule comprising β-galactose, to the solid support may be selected from among known methods. Such methods are also provided by the manufacturers of the solid supports. In one embodiment, the β-galactose-linked solid support is loaded in an affinity column for separation, isolation and/or purification of the target. In this embodiment, a sample containing the purification target (e.g., lysate from an AAV production culture) is allowed to flow through the column so that the purification target specifically binds to the β-galactose-linked solid support. Thereafter, the column is washed to remove non-specifically bound material, while retaining the specifically bound purification target. Desirably, the wash reagent is saline, or another suitable reagent, which is buffered to physiologic pH (e.g., phosphate buffered saline). The column is then subjected to a further washing step under conditions which remove the purification target. Suitably, the elution reagent is a solution containing high concentrations of salt. One suitable example, is a phosphate buffered saline solution containing NaCl at concentrations of at least about 0.1M. Another suitable solution contains phosphate buffered saline and at least about 0.4 M NaCl. Given this information, one of skill in the art can readily select an alternative salt solution which will achieve similar effect. Alternatively, the elution reagent may be any suitable acidic reagent, or salt thereof, (e.g., a reagent having a low pH in the range of about 1 to about 5. Examples of such reagents include acetic acid (e.g., 1 mM) and salts thereof such as sodium acetate, and 0.1 M glycine (pH 3), among others which will be readily apparent to those of skill in the art. Following elution of the purification target (e.g., having an AAV9 cell binding domain), the AAV may be subject to concentration by conventional techniques.

In another embodiment, the β-galactose-linked solid support may be incubated with a sample containing the purification target. In such an embodiment, the sample may be a solution containing the lysate from a cellular culture in which the protein to be isolated was produced. Alternatively, the sample may be a biological sample from a subject, or a biological sample from a subject in admixture with a suitable diluent. The "biological samples from a subject" of the invention can include any sample includes, among other fluids, whole blood, plasma or serum, where the formed bodies are cells, particularly blood cells. Such samples may be purified by conventional methods, such as separation by centrifugation, etc., for the handling of other samples of that type. These "biological samples from a subject" may be mixed with labeling compounds and/or mixed with optionally buffers or diluents in order to adjust the concentration of the sample, or otherwise prepare the sample for analysis. In yet another alternatively, the biological sample may be a tissue sample, and the β-galactose linked solid support may be admixed with a suitable buffer or other diluent for incubation with the tissue sample.

In another embodiment, the invention provides a kit useful for separating the purification target. This kit is particularly well adapted for use in production of viral vectors (e.g., a clade F, or AAV vector containing an AAV9-cell binding domain in its capsid).

Typically, such a kit contains a solid support having β-galactose or a β-galactose containing molecule linked thereto. Such solid supports may be selected from among these described above. In one desirable embodiment, the solid support is a bead or gel for incubation with the sample. In another desirable embodiment, the solid support is loaded in an affinity column (e.g., a liquid chromatography column), and the sample is passed through the column.

In addition, a kit of the invention may also contain the desired reagents, including wash reagents, elution reagents, and concentration reagents. Such reagents may be readily selected from among the reagents described herein, and from among conventional concentration reagents. In one desirable embodiment, the wash reagent is an isotonic saline solution which has been buffered to physiologic pH, such as phosphate buffered saline (PBS); the elution reagent is PBS containing 0.4 M NaCl, and the concentration reagents and devices. For example, one of skill in the art will recognize that reagents such as polyethylene glycol (PEG), or $NH_4SO_4$ may be useful, or that devices such as filter devices. For example, a filter device with a 100 K membrane would concentrate rAAV.

These kits may additionally contain reagents necessary to maintain or preserve the samples. More importantly, the kit contains instructions for performing the competitive assay and preparing the controls. Also provided in a kit may be suitable diluents and buffers for the samples, indicator charts for signal comparisons, disposable gloves, decontamination instructions, applicator sticks or containers, and sample preparator cups. The kits preferably also contain necessary buffer substances or media, as required. One of skill in the art could assemble any number of kits with the information and components necessary to perform the method on a patient for any specific receptor and target cell, and compare the results to norms for that binding site.

In still another embodiment, the invention provides a kit useful for detecting the presence of the purification target (e.g., AAV9) in a sample. In addition to containing the components described above, such a kit may also contain a marker reagent which permits visual detection of binding of the purification target to the molecule. This kit is particularly well adapted for detection of purification target in a biological sample from a subject, e.g., the blood. This type of kit, in addition to containing the β-galactose-linked support and reagents described above, may further include markers which are visually detectable.

The term "markers" generally refers to molecules, preferably proteinaceous molecules, but also small chemical molecules, preferably those which are visually detectable. In one example, these markers enable detection by emitting a detectable signal of a particular wavelength upon excitation by a laser. Phycobiliproteins, tandem dyes, certain fluorescent proteins, small chemical molecules, and certain molecules detectable by other means can all be considered markers for these analyses. See, e.g., the markers listed in *Handbook of Fluorescent Probes and Research Chemicals*, 6th Ed., R. P. Haugland, Molecular Probes, Inc., Eugene, Oreg. (1996).

Examples of phycobiliproteins useful in the present invention are phycocyanin, allophycocyanin (APC), allophycocyanin B, phycoerythrin (PE) and preferably R-phycoerythrin. PE is among the brightest fluorescent dyes currently available. Conjugated to an antibody, PE has been used to detect interleukin-4 in a fluorescent plate assay and in (M C Custer and M T Lotze, (1990) *J. Immunol. Meth.*, 128, 109-117) and found to be the only tested fluorophore that produced adequate signal. The tandem dyes are non-naturally occurring molecules that may be formed of a phycobiliprotein and another dye. See, for example, U.S. Pat. Nos. 4,542,104 and 5,272,257. Examples of tandem dyes useful in the present invention are phycoerythrocyanin or PC5 (PE-Cy5, phycoerythrin-cyanin 5.1; excitation, 486-580 nm, emission, 660-680 nm) [A. S. Waggoner et al, (1993) *Ann. N.Y. Acad. Sci.*, 677:185-193 and U.S. Pat. No. 5,171,846] and ECD (phycoerythrin-texas red; excitation, 486-575 nm, emission, 610-635 nm) [U.S. Pat. Nos. 4,542, 104 and 5,272,257]. Other known tandem dyes are PE-Cy7, APC-Cy5, and APC-Cy7 [M. Roederer et al, (1996) *Cytometry*, 24:191-197]. Tandem dyes, PC5 and ECD, have been successfully directly conjugated to monoclonal antibodies by several methods that involve iminothiolane activation of the dye. Still other markers which may be directly conjugated to a ligand and used with the phycobiliproteins or tandem dyes in this invention to add additional numbers of markers (labeled ligands) to the method include small molecules which upon excitation emit wavelengths of less than 550 nm. Such molecules do not overlap with the emissions of the phycobiliproteins. One example of such a marker is fluorescein isothiocyanate (FITC). Others are listed in the Handbook cited above. Still other markers which may be employed in this method to provide additional colors are the proteins known as the green fluorescent proteins and blue fluorescent proteins; also useful may be markers which emit upon excitation by ultraviolet light. The biliproteins and tandem dyes are commercially available from various sources including Coulter International Corporation, Miami, Fla., Molecular Probes, Inc., Eugene, Oreg. and Prozyme, Inc., San Leandro, Calif. The other markers or labels discussed above may be obtained commercially from known sources.

The methods for utilizing these markers will be readily apparent to those of skill in the art, and may involve incubating the sample in the presence of a marker prior to contacting the β-galactose-linked solid support. Alternatively, the marker may be bound to the solid support. In yet another alternative, the marker may be incubated in the eluate containing the purification target following the wash step which removes the specifically bound purification target from the solid support. The selection of the marker and the detection system are not a limitation of the present invention. The kits provided by the present invention are useful for performing the methods described herein.

The following examples are illustrative only and are not intended to be a limitation on the scope of the invention.

IV. EXAMPLES

Example 1—Cell Binding and Transduction Assays

A. Binding Assays

For binding assays, cells were scraped from 150 cm$^2$ flasks and seeded onto 96-well plates at 5×10$^5$ cells/well in 100 µl cold serum-free (SF) media. AAV vectors were produced as previously described by Penn Vector (www.med.upenn.edu/gtp/-vector_core.shtml) and were added at 5×10$^9$ genome copies (GC)/well in 100 µl cold SF media and incubated at 4° C. for 1 hr. Cells were washed three times with SF media and resuspended in 200 µl PBS. Total DNA was extracted using the QIAamp DNA Mini kit (QIAGEN). Cell-bound GCs were quantified by real-time PCR. Primers and probe used were complementary to the SV40 polyA sequence of the vector genome. F primer: AGCAATAGCATCACAAATTTCACAA [SEQ ID NO: 2]; R primer: CCAGACATGATAAGATACATTGATGAGTT [SEQ ID NO: 3]; TaqMan probe: 6FAM-AGCATTTTTTT-CACTGCATTCTAGTTGTGGTTTGTC [SEQ ID NO: 4]-TAMRA. For cell transduction assays, cells were seeded at $10^5$ cells/well in black-walled, clear-bottom 96-well plates overnight. Plates were then placed at 4° C. for 15 min and $10^9$ GC of AAV vector expressing ffLuc was added in 100 µl cold SF media and incubated for 1 hr at 4° C. Cells were then washed three times with SF media. Warm media containing serum was supplemented and cells were incubated at 37° C. for 48 hrs. ffLuc expression was monitored by adding 150 µg/ml D-luciferin substrate per well and measuring the relative light units/second (RLU/s) using a luminometer.

B. Cell Transduction Assays

For cell transduction assays, cells were scraped from 150 $cm^2$ flasks and seeded at $5 \times 10^5$ cells/well in black-walled, clear-bottom 96-well plates overnight. Plates were then placed at 4° C. for 15 min and $10^9$ GC of AAV vector expressing ffLuc was added in 100 µl cold SF media and incubated for 1 hr at 4° C. Cells were then washed three times with SF media. Warm media containing serum was supplemented and cells were incubated at 37° C. for 48 hrs. ffLuc expression was monitored by adding 150 µg/ml D-luciferin substrate per well and measuring the relative light units/second (RLU/s) using a luminometer.

C. In Vivo Experiments

AAV with or without 100 mU NA in 50 µl PBS. NA was administered either 1 hr prior or simultaneously with vector instillation. nLacZ gene expression in the lungs was examined 21 days post-administration by methods previously described [Bell, et al, Histochem Cell Biol, 124 (6): 2427-35 (2005)]. Lung sections were examined at both 100× and 200× magnification. LacZ positive cells in the conducting airways were quantified by counting positive cells per 200× magnification field of view. Mice were anesthetized with ketamine/xylazine and given an intranasal instillation of 100 mU NA in 30 µl PBS or PBS alone as control. Lungs were harvested 1 hr later by methods previously described (Bell, 2005, cited above) and sections fixed in cold (−20° C.) acetone for 5 min. The lung sections were then blocked with Carbo-Free™ Blocking Solution (Vector laboratories) and incubated with 15 µg/ml rhodamine labeled Ricinus Communis Agglutinin I (RCA I) and 7.5 µg/ml fluorescein labeled Sambucus Nigra Lectin (SNA) for 30 min at room temperature. Slides were then washed twice in PBS and mounted in Vectashield with DAPI (Vector laboratories). Images were taken by both wide field (200×) and confocal microscopy (Zeiss LSM 510 confocal microscope). For RCA staining of muscle, heart, liver, and brain, organs were removed from untreated mice and sections stained as above. For CD31 staining of brain, slides 48 were incubated with rat anti-CD31 primary antibody (BD Pharmingen) followed by fluorescein labeled anti-rat secondary antibody (Vector Laboratories) and rhodamine labeled RCA. For α-tubulin staining of lung, slides were processed as above, except sections were fixed in 4% paraformaldehyde and stained with mouse anti-α-tubulin primary antibody (Sigma) followed by fluorescein labeled horse anti-mouse secondary antibody (Vector Laboratories) and rhodamine labeled RCA. Images were taken at 400× magnification. Statistical significance was determined using Student's 2-tailed t test. P values of less than 0.001 were considered significant. Data are represented as mean±SD.

Example 2—Glycosidase Treatment and Lectin Competition

Pro-5 cells were treated with 50 mU/ml of NA type III from Vibrio cholerae (Sigma) in 100 µl SF media or control cells with media alone for 2 hrs at 37° C. Some cells were then additionally treated with 60 mU/ml β-(1,4)-galactosidase in 50 µl reaction buffer (Sigma) or control cells with reaction buffer alone for 3 hrs at 37° C. Cells were then washed three times before the binding and transduction studies, as described above. For lectin competition studies, Pro-5 cells were first treated with NA to remove sialic acid. Cells were washed with cold SF media and lectins were added at 50 µg/ml in 100 µl SF media or media alone as a control and incubated at 4° C. for 15 min. The lectin solution was then removed and a mixture of AAV vector ($5 \times 10^9$ GC for binding assays and $10^9$ GC for transduction assays) and 50 µg/ml lectin or vector alone as control was added and incubated at 4° C. for 1 hr. Cells were then washed and analyzed for AAV binding or transduction as described above. Lectins used in the study include *Erythrina Cristagalli* Lectin (ECL), which binds galactosyl (β-1,4) N-acetylglucosamine, *Ricinus Communis* Agglutinin I (RCA I), which binds terminal galactose residues, Wheat Germ Agglutinin (WGA), which binds N-acetylglucosamine and also interacts via sialic acid, *Hippeastrum* Hybrid Lectin (HHL), which binds (α-1,3) and (α-1,6) mannose, *Griffonia Simplicifolia* Lectin I isolectin B4 (GSL B4), which binds α-galactose, and *Lotus Tetragonolobus* Lectin (LTL), which binds α-linked fucose (Vector Laboratories).

Example 3—Screening of Glycan Binding Specificity of AAV9

For glycan microarray (GMA) binding studies virus like particles (VLPs) of AAV9 were prepared using the Bac-to-Bac baculovirus expression system/Sf9 expression system as previously described [Mitchell, et al, 2004, *PLoS Biol* 2(8): E234] and screened in a high-throughput glycan microarray developed by Cores D and H of the Consortium for Functional Glycomics (CFG; an NIH National Institute of General Medicine Science Initiative). The printed array (Mammalian Printed Array [PA] V4.1, www.functionalglycomics.org/static/consortium/resources/resourcecoreh14.shtml) was composed of 465 different natural and synthetic mammalian glycans, including sialylated sugars with different linkages and modifications which was generated using amine coupling to covalently link amine-functionalized glycans or glycanconjugates to an amine-reactive N-hydroxysuccinimide-activated glass slide. A printed slide, containing six replicates per glycan or glyco-conjugate, was incubated with AAV9 VLPs at 200 µg/ml, then ADK9, a capsid monoclonal antibody (provided by Jurgen Kleinschmidt, German Cancer Research Centre, Heidelberg, Germany) was overlaid on the bound capsids, followed by a FITC-labeled secondary antibody (at 5 µg/ml) for detection. Fluorescence intensity was detected using a ScanArray 5000 confocal scanner (Perkin Elmer Inc.). IMAGENE image analysis software (BioDiscovery, El Segundo, Calif.) was utilized to analyze the image. The relative binding for each glycan was expressed as mean relative fluorescence units (RFU) of four of the six replicates, calculated without using the highest and lowest values. The binding data was analyzed using two selection criterion: (I) Glycans that were within 3 standard deviations of the mean of the glycan with the highest RFU value and (II) Glycans with coefficient of variation (% CV) of <20% between the RFUs of the four replicates used to calculate the average RFU value (with % CV=coefficient of variation, defined as the ratio of the standard deviation of the data to the mean expressed as a percentage). Information relevant to the generation of the glycan array data is available on the open-access website at the following URL/accession site: www.functionalglycomics.org/glycomics/

HServlet?operation=view&sideMenu=no&psId=primscreen_3528. Included in this data set are the raw data, the normalized data, sample annotation, experimental design, annotation of the glycan array and experimental protocols (accession id primscreen_3528).

Results

As described herein, several previously described AAVs (serotypes 1, 2, 5 and 6) and the novel AAV serotypes 7, 8, 9 and rh32.33 were screened for binding to the CHO cell line Pro-5, which is used to study the genetics and biochemistry of glycosylation, with and without treatment with exo-β-sialidase (neuraminidase, NA). Results with the first generation AAVs were as expected in that NA pretreatment (FIG. 1A) had no effect on binding of AAV2 and binding of AAV1, AAV5, and AAV6 was diminished by at least two logs (FIG. 1B). Studies with the novel AAVs failed to show an effect of NA treatment on binding of AAV7, 8, and rh32.33 while AAV9 showed an unexpected 2.5 log increase in binding (FIG. 1B).

The inventors speculated that the presence of terminal SA on an oligosaccharide either inhibited binding to AAV9 or that the removal of SA exposed a molecule that enhanced binding. It was considered that the most likely candidate would be β-1,3 or β-1,4 galactose which is the penultimate monosaccharide on most SA-rich glycans (FIG. 1A). These hypotheses were initially explored using somatic cell mutants of the parent CHO cell line, Pro-5, which are deficient in various enzymes involved with glycosylation by virtue of lectin resistance [S K Patnaik and P. Stanley (2006) Methods Enzymol 416:159-182]. Lec-2 is deficient in CMP-SA golgi transporter and should have a full complement of N and O-glycans that are missing terminal SA (FIG. 1A). Lec-8 is deficient in UDP-Gal golgi transporter which should produce N- and O-glycans that are missing both SA and galactose saccharides (FIG. 1A). Vectors based on AAVs 2, 6, and 9 expressing firefly luciferase (ffLuc) were incubated with Pro-5, Lec-2 and Lec-8 cells and analyzed for binding and transduction (FIG. 2A, B). Binding and transduction of AAV2 was the same in all three cell lines and decreased with AAV6 in Lec-2 and Lec-8 cells relative to Pro-5 cells which is expected based on previous studies demonstrating the importance of SA in facilitating AAV6 entry. For AAV9, binding and transduction increased substantially in Lec-2 but decreased to baseline levels in Lec-8 cells which is more consistent with the hypothesis that binding to terminal β-galactose facilitates uptake rather than that SA inhibits uptake. The concurrence of binding with transduction suggests that binding to terminal galactose is the rate-limiting step in AAV9 transduction. The impact of eliminating sialic acid was greater on binding than on transduction suggesting post entry steps may also limit transduction.

The role of terminal galactose in AAV9 binding was further studied in Pro-5 cells that were pre-treated with NA and then co-cultured with lectins of different specificities (FIG. 2C, binding; FIG. 2D, transduction). The only lectins that blocked binding of AAV9 were *Erythrina Cristagalli* Lectin (ECL) which recognizes β-1,4 galactose and *Ricinus Communis* Agglutinin I (RCA I) which recognizes several types of β-galactose linkages with β-1,4 galactose showing the highest affinity; neither affected binding of AAV2. Lectins that recognize α-galactose [*Griffonia Simplicifolia* Lectin I isolectin $B_4$ (GSL $B_4$)], α-1,3 and α-1,6 mannose [*Hippeastrum* Hybrid Lectin (HHL)] and α-fucose [*Lotus Tetragonolobus* Lectin (LTL)] did not interfere with binding of AAV2 or AAV9. Wheat Germ Agglutinin (WGA) had a slight effect on AAV9 binding likely due to its interaction with N-acetylglucosamine which is commonly bound to galactose. Lectin inhibition of AAV2 and AAV9 transduction confirmed the binding results except for RCA which was not informative since it was toxic to cells.

A final confirmation of the glycan specificity of AAV9 uptake was performed in Pro-5 cells pretreated with NA to cleave terminal SA or NA and β-galactosidase (β-gal) that would remove both NA and β-galactose saccharides (FIG. 1A). Binding and transduction with AAV2 was unaffected by enzyme pretreatment while NA enhanced transduction of AAV9 as described earlier, an effect that was reversed by subsequent treatment with β-gal (FIG. 2E, F).

The glycan-capsid interactions of AAV9 were further interrogated using a glycan microarray composed of 465 different natural and synthetic mammalian glycans which contains 6 replicates for each glycan. A similar strategy was used to verify the binding of AAV1 to sialylated glycans as determined by biochemical and molecular approaches (Wu et al., 2006, J Virol, 80: 9093-9103). In our analysis, each glycan was evaluated for binding as measured by relative fluorescent units (RFU) in terms of the mean of four replicates within the array ±1 SD (the highest and lowest binding within the six replicates were eliminated). Variation within the 4 replicates was assessed as the % CV which was considered low if it was less than 20. The selection of glycans with specific binding affinity for AAV9 capsids was based on two independent criteria; high overall total binding as measured by RFU and low variation between the 4 replicates as assessed by % CV. The highest binding glycans were arbitrarily defined as those with mean RFU values that fell within 3 S.D. of the highest binding glycan 415. Of the four glycans that fulfilled the criteria of high binding affinity, three showed high specificity as measured by % CV less than 20. These three glycans, 415, 297 and 399, demonstrated sufficient affinity and specificity to be considered potential receptors for AAV9 binding. The three glycans selected as being specific for binding to AAV9 based on total binding and specificity of binding were all shown to have terminal galactose (Gal) with either β-1,4 linkages (415 and 399) or a β-1,3 linkage (297). Each glycan contains Galβ1-4(Fuc α1-3)GlcNAc linked β1-3 or β1-6 to GalNAc in their structures suggesting a structural context of the sialic acid deficient glycan for binding to AAV9. Reconciling the binding data with cell based binding/transduction experiments confirms the role of terminal β-galactose linkages in tropism of AAV9.

As described herein, studies were performed in mice to determine whether transduction of conducting airway with AAV9 could be enhanced by pre-treating mouse airways with a formulation that contained NA. Comparisons were made to mice administered with AAV6 which in previous studies showed efficient in vivo transduction of conducting airway, [M P Limberis, et al, (2009) Mol Ther 17:294-301] which based on in vitro studies with cell lines, may be dependent on binding to SA [Z. Wu, et al., (2006) *J Virol* 80:9093-9103]. Lung delivery of AAV9 in the absence of NA demonstrated the expected pattern of alveolar restricted transduction; administration of NA into the lung 1 hr prior to or at the time of AAV9 administration yielded a very different pattern with high level transduction in both the alveolar and conducting airway epithelial cells. The high level transduction of conducting airway obtained with AAV6 was completely eliminated when animals were treated with NA confirming the dependence of in vivo transduction on binding to SA. The consequences of airway delivery of NA on the abundance and distribution of glycan structure was studied directly by staining lung sections with fluorescent labeled lectins that bind terminal galactose residues (RCA) or terminal SA residues (SNA). Prior to NA treatment, staining with RCA was limited to alveolar cells and the basal lateral region of conducting airways. A similar pattern is observed with SNA although the apical surface of the conducting airway was also stained. Treatment with NA had the most dramatic result on the staining of conducting airway epithelial cells which was substantially increased with respect to RCA and moderately reduced to SNA.

Higher resolution microscopic studies were performed to determine if RCA binding localized to the plasma membrane or the overlying mucus layer. Lung sections from animals pre-treated with NA were evaluated for co-localization of RCA staining with immune-localization of α-tubulin, which delineates the cilia from the apical surface of airway epithelial cells. These studies demonstrated binding of RCA to the cell surface of epithelial cells in the conducting airway of NA pretreated lungs.

A major impediment to transduction following intravascular (IV) administration of AAV vectors is the physical barrier of the contiguous endothelium and basal lamina of the microcirculation. The one exception is the liver which contains fenestrated endothelia allowing direct access of vector in blood to the hepatocytes. AAV9 is unique in that it partially overcomes this barrier allowing targeting of skeletal and cardiac muscle and, to a lesser extent, cells of the central nervous system (Inagaki, K., S. et al. (2006), *Mol Ther* 14(1): 45-53.; Duque, et al., (2009) Mol Ther 17:1187-1196; K. D. Foust, et al, (2009), Nat Biotechnol 27:59-65). lacZ transduction was analyzed following IV administration of AAV9 vector at doses of $10^{11}$ and $10^{12}$ genome copies (GC)/mouse. This was correlated with the presence of terminal β-galactose through staining with RCA. As has been described, liver is efficiently transduced at even low doses of vector [Vandendriessche, et al, 2007, *J Thromb Haemost* 5(1): 16-24)]; it is possible to efficiently transduce cardiac and skeletal muscle at higher vector doses [Inagaki, 2006, cited above]. Surfaces of muscle fibers from skeletal and cardiac tissues demonstrated high levels of terminal β-galactose as evidenced by binding to RCA. Hepatocytes demonstrated lower levels of RCA binding although endothelial surfaces of hepatic vessels stained brightly.

Lectin binding studies of brain tissues were notable for substantial binding of RCA but not SNA to endothelial cell. This is intriguing since AAV9 has the unique property of targeting cells of the CNS after intravenous injection although efficient transduction is achieved with both AAV9 and AAV5 when directly injected into the brain [B. L. Davidson, et al., (2000) Proc Natl Acad Sci USA 97:3428-3432; S.]. A major impediment to CNS delivery of therapeutics following systemic administration is the blood brain barrier which is formed from a uniquely tight network of endothelial cells. Receptor and absorptive-mediated transcytosis pathways across the endothelium have been exploited to overcome this barrier. The high levels of the AAV9 receptor found on the micro-circulation of the brain may play a role in its ability to target the CNS through transcytotic pathways.

The potential role of glycans in mediating AAV9 transduction was the focus of this study since they often serve as receptors for virus infection usually with exquisite specificity with respect to the component monosaccharide. Specific interactions with glycans containing terminal sialic acid have been described for many viruses including several other AAV serotypes. Our finding that binding and transduction by AAV9 occurs via terminal β-galactose linkages has not been described for any other virus including the known AAVs, although Norovirus binds to glycans with α-galactose linkages (Zakhour, M., (2009). The alphaGal epitope of the histo-blood group antigen family is a ligand for bovine norovirus Newbury2 expected to prevent cross-species transmission. *PLoS Pathog* 5(7): e1000504.).

Glycan array studies demonstrated specific binding of AAV9 to 3 glycans, all of which contained terminal β-galactose linkages confirming the importance of this saccharide in transduction as was delineated in multiple cell lines using three independent approaches (i.e., glycosidase pre-treatment, lectin competition and somatic cell mutants). These glycans all contained Galβ1-4(Fucα1-3) GlcNAc linked β1-3 or β1-6 to GalNAc in their structures and were linked via threonine through a GalNAc, indicating that O-linked galactose containing glycans are capable of binding to AAV9 although functional interactions with glycans associated with other types of linkages cannot be ruled out (Marth, J. D. 1999. O-Glycans. Essentials of Glycobiology. A. Varki, R. Cummings, J. Eskoet al. Cold Spring Harbor, N.Y., Cold Spring Harbor Laboratory Press: p. 101-113.). An important caveat regarding the binding data is that binding affinity does not necessarily correlate with functional significance in terms of glycosylated receptors that mediate transduction. The receptors for important gene therapy vectors have been well characterized in vitro but rarely has the significance of these receptors for in vivo transduction been confirmed. One example of a discordance between in vitro and in vivo transduction is that of human adenovirus 5 (Ad5). The coxsackie virus and adenovirus receptor (CAR) was isolated as the receptor for Ad5 based on in vitro studies and attempts to confirm the importance of CAR following in vivo gene transfer utilized CAR-binding ablated Ad5. Following intravenous administration, the transduction levels and the liver-selective profile of CAR-binding ablated Ad5 vectors were similar to Ad5 suggesting potential redundant uptake pathways in vivo. Investigation of the mechanism of Ad5 transduction in vivo determined that the presence of blood coagulation factors could mediate transduction through a non-CAR-dependent pathway. In comparison, our studies with AAV9 vectors following lung-directed gene transfer in combination with NA provided direct confirmation of the importance of β-galactose linkages in transduction of conducting airway epithelial cells by AAV9.

Evaluating the role of β-galactose linkages in transducing cells of tissues other than the lungs following in vivo gene transfer is more complicated due to barriers of delivery that are not present when vector is delivered into the airway allowing direct access to epithelial cells. Transduction following IV administration of AAV9, which is a route of administration being considered in many clinical applications of gene therapy, illustrates this point. IV infusion of vectors based on most AAV serotypes results in transduction primarily limited to hepatocytes because the fenestrae of the hepatic sinusoids eliminate the vascular barrier. In our studies, AAV9 efficiently transduces hepatocytes despite limited levels of β-galactose. Higher doses of AAV9 can overcome the vascular barrier and efficiently transduce cardiac and skeletal muscle fibers that do contain high levels of cell surface β-galactose glycans. As noted by several groups, AAV9 uniquely traverses the even more fortified blood brain barrier to allow limited transduction of neurons. It was speculated that the presence of glycans with β-galactose linkages on the surface of endothelial cells of some vascular structure, as we have shown in the brain, may be involved in facilitating this egress possibly through a process of transcytosis. The demonstrated binding of AAV9 to O-linked glycans of diverse structures suggests that interactions with non-cell mediated glycoproteins such as in blood or in mucosal surfaces may modulate bio-distribution of vector and transduction profiles.

Identification of the primary receptor for AAV9 was also useful in developing a pharmacologic approach for enhancing its transduction in conducting airway of the lung. The effect is expected to be achieved for other targets of AAV9 particularly when the NA-formulated vector can be administered directly into tissue such as the retina or into a closed space such as a joint.

Example 5—Identification of Galactose Binding Domain of the AAV9 Capsid

In this study, we aimed to identify the specific amino acids of the AAV9 capsid necessary for binding to galactose. By site-directed mutagenesis and cell binding assays, plus computational ligand docking studies, we discovered five amino acids required for galactose binding that form a pocket at the base of the protrusions around the icosahedral 3-fold axes of symmetry. The importance of these amino acids was also confirmed by in vivo studies in the mouse lung. Identifying the interactions necessary for AAV9 binding to galactose may lead to advances in vector engineering.

In this study, we sought to identify the galactose binding motif on the AAV9 capsid. We generated a series of alanine mutants to determine the necessity of specific amino acids for galactose binding both in vitro and in vivo. This led to the discovery of a galactose binding pocket at the base of the protrusions that surround the 3-fold axes of symmetry of the AAV9 capsid, which was also confirmed by molecular docking studies.

A. Materials and Methods

1. Cells Lines.

All cell lines were obtained from the American Type Culture Collection (ATCC). Three different Chinese Hamster Ovary (CHO) cell lines were used in binding and transduction experiments, including the parental cell line Pro-5, the sialic acid deficient cell line Lec-2, and the galactose-deficient cell line Lec-8. These cells were cultured in α-minimum essential medium (α-MEM) supplemented with ribonucleosides and deoxyribonucleosides (Invitrogen) with 10% fetal bovine serum (FBS) and 1% penicillin/streptomycin.

2. Animals.

Male C57BL16 mice (6-8 weeks old) were purchased from Charles River Laboratories and housed in the Animal Facility of the Translational Research Laboratories at the University of Pennsylvania. All animal procedures were approved by the Institutional Animal Care and Use Committee of the University of Pennsylvania.

3. AAV9 Mutagenesis and Small-Scale Vector Preparation.

Figure 3A:
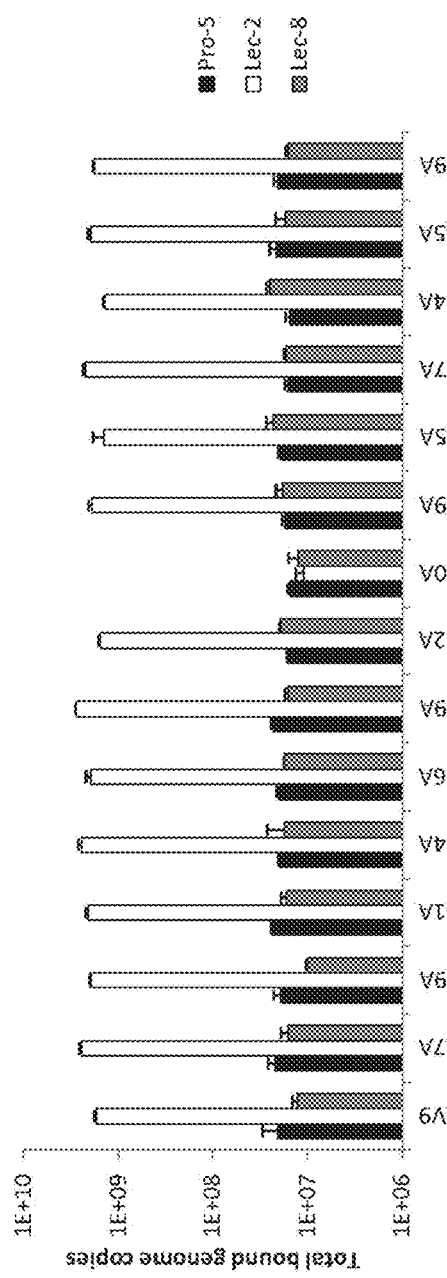
Figure 3B:
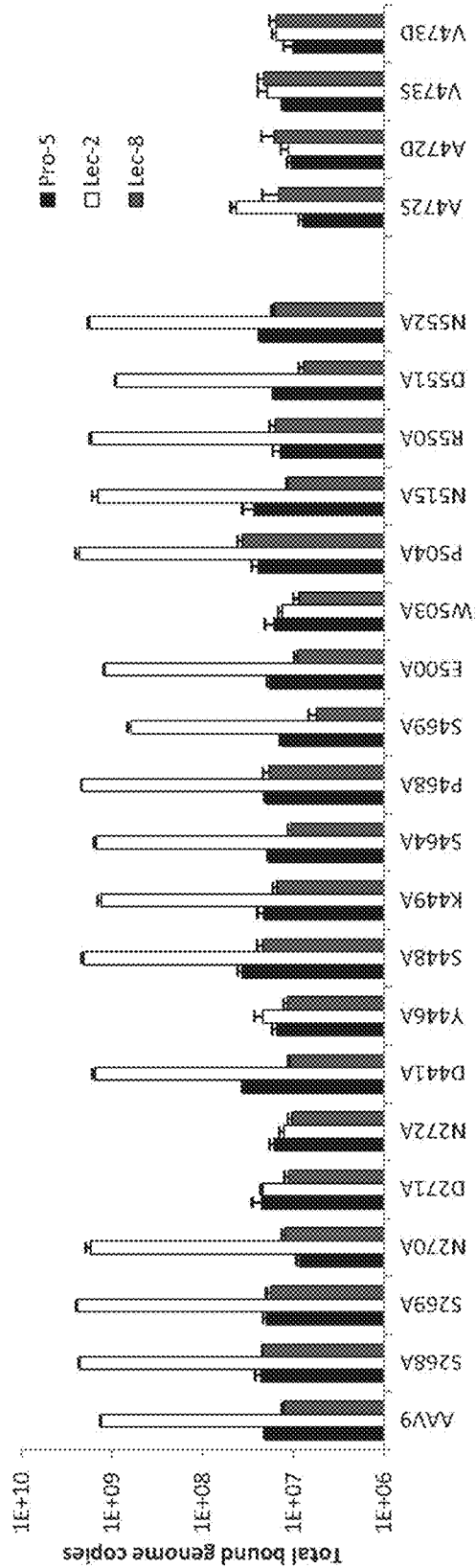

Specific charged or polar amino acids of the AAV9 capsid sequence were chosen for mutation to nonpolar alanine, as indicated in FIGS. 3A-3B. Mutagenesis was performed using the QuikChange Lightning Site-Directed Mutagenesis Kit from Agilent Technologies. For subsequent small-scale production of mutant vectors for use in in vitro binding and transduction assays, triple transfection of HEK293 cells in 6-well plates (9.6 cm$^2$) was performed using a plasmid expressing the AAV2 rep gene and the mutant AAV9 cap gene, as well as plasmids expressing the ffLuc transgene expressed from a cytomegalovirus (CMV) promoter flanked by the AAV2 inverted terminal repeats, and an adenovirus helper plasmid (pAdΔF6). Cells and supernatant were harvested after 72 hours in 2 ml total media and subjected to three freeze/thaw cycles and then centrifuged at 3500×g for 30 min to remove cell debris. The titers of the vectors (GC/ml) were determined by quantitative PCR.

4. Vector Production and Purification for in Vivo Studies.

AAV vectors for use in vivo were produced and purified by Penn Vector as described: www.med.upenn.edu/gtp/vector_core/production.shtml. A plasmid expressing nLacZ from a chicken β-actin promoter and flanked by AAV2 inverted terminal repeats was packaged by triple transfection of HEK293 cells with plasmids encoding the AAV2 rep gene and the AAV9 or mutant cap gene, and an adenovirus helper plasmid (pAdΔF6). Vectors were purified by iodixinol gradient centrifugation and titers determined by quantitative PCR.

5. Cell Binding and Transduction Assays.

Figure 4A:
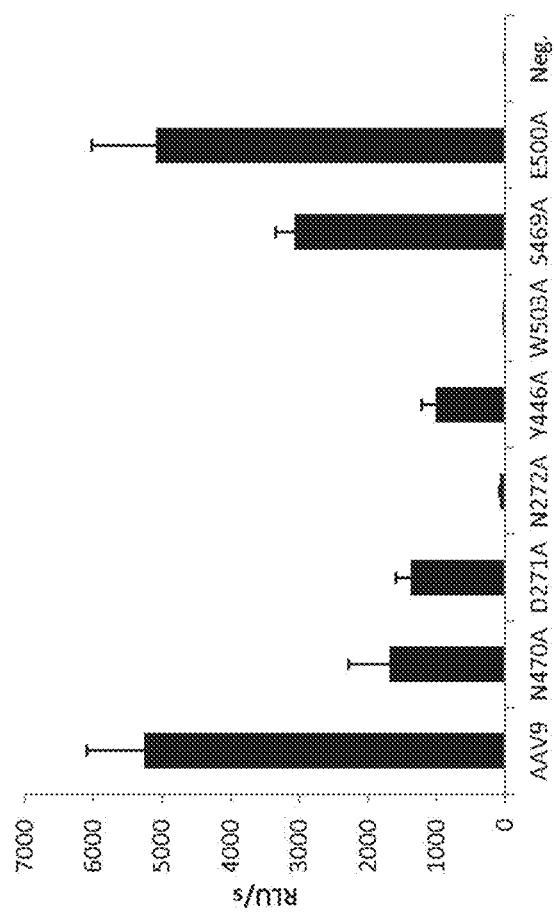
Figure 4B:
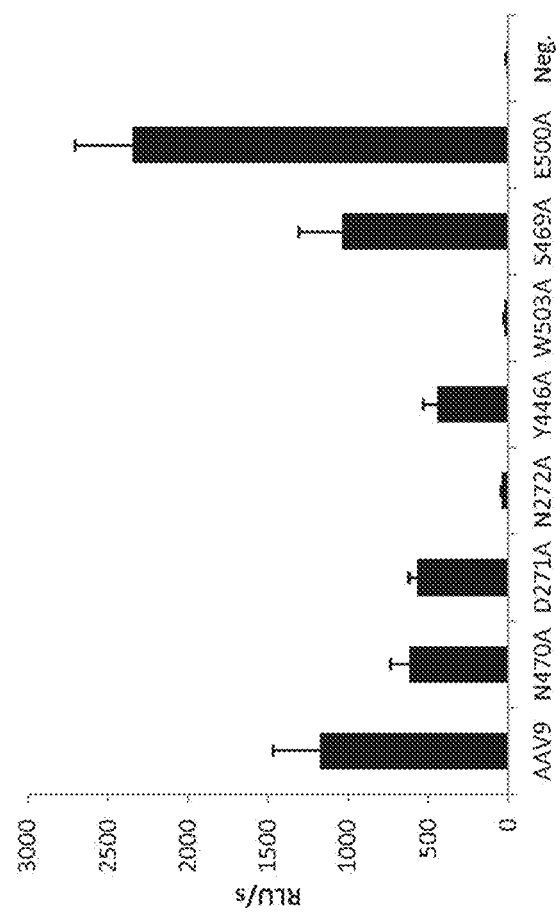

For binding assays, Pro-5, Lec-2, and Lec-8 cells were scraped from 150 cm$^2$ flasks and seeded at 5×10$^5$ cells/well in 96-well plates in 100 µl cold serum-free α-MEM. Vectors were added at 5×10$^9$ GC/well in 100 µl cold α-MEM and incubated at 4° C. for one hour. Then, cells were washed three times with 200 µl α-MEM and resuspended in 200 µl PBS. Total DNA was extracted using the QIAamp DNA Mini Kit (QIAGEN) and cell-bound vector GCs were determined by quantitative PCR. For transduction assays, 10$^5$ cells/well were seeded in black-walled, clear-bottom 96-well plates overnight. After removal of the media, AAV vector expressing ffLuc (10$^9$ GC) was added to the cells in 100 µl complete media and incubated at 37° C. for 48 hours. ffLuc expression was then determined by adding 150 µl g/ml D-luciferin substrate per well in 100 µl α-MEM and measuring the relative light units/second (RLU/s) using a luminometer. The in vitro transduction efficiency of mutant vectors is shown in FIGS. 4A and 4B.

6. Transduction of Mouse Lung.

As described in Example 3, mice were anesthetized with ketamine/xylazine and given an intranasal instillation of 100 mU NA in 30 µl PBS. One hour later, 10$^{11}$ GC of AAV9 or mutant vector expressing nLacZ was delivered intranasally in 50 µl PBS. Twenty-one days post-administration, β-gal expression in the lungs was examined by methods previously described (Bell, 2005, cited above). Lung sections were examined at 100× magnification.

7. Prediction of the Galactose Binding Site on the AAV9 Capsid by Molecular Docking Studies.

Molecular docking was performed to predict the galactose binding site on the AAV9 capsid using the molecular docking webserver PatchDock (bioinfo3d.cs.tau.ac.il/PatchDock/index.html) (Schneidman-Duhovny, et al., Nucleic Acids Res 33 (Web Server issue): W363-7 2005). The x-ray crystal structure for galactose bound to human galectin-3, PDB accession #1A3K was utilized to provide the coordinates for galactose (Seetharaman, et al., J Biol Chem, 273 (21): 13047-52 (1998). The coordinates for the AAV9 x-ray crystal structure (unpublished data) were used to build a trimer using VIPERdb Oligomer generator(viperdb.scripps.edu/oligomer_multi.php) (Carrillo-Tripp, Nucleic Acids Res, 37 (Database issue): D436-42 (2009). The output PDB file for the AAV9 trimer was truncated to include amino acids that were surface accessible and maintained the structural integrity of the viral capsid surface loops. The amino acids included in the truncated AAV9 trimer PDB file as the input file for molecular docking were N262-Y277, L435-G475, and F501-M559. Molecular docking was performed in an undirected fashion to evaluate the site on the AAV9 capsid that was likely to interact with galactose. Docking was also performed using the truncated AAV9 trimer and sialic acid. The X-ray crystal structure for Equine Rhinitis A Virus in complex with its sialic acid receptor, PDB accession #2XBO, was utilized to provide the coordinates for sialic acid (Fry, et al. J Gen Virol, 91(Pt8): 1971-7 (2010).

B. Results

1. N470 is Necessary for AAV9 Galactose Binding

To identify potential amino acids of the AAV9 capsid that could be involved in galactose binding, the capsid amino acid sequence of AAV9 was aligned to that of other serotypes that do not bind galactose, such as AAVs 1, 2, 6, 7, and 8, to determine which amino acids are unique to AAV9. Based on this alignment, 14 amino acids that have either polar or charged side chains were chosen for mutation to non-polar alanine to examine the effect on AAV9 binding (FIG. 3A). These mutant capsid constructs were used to make vector by small-scale preparation methods and yielded similar titers compared to wild type AAV9.

The mutant vectors were then added to three different CHO cell lines to assess their binding capabilities. The parental CHO cell line Pro-5, as well as somatic cell glycosylation mutants of this cell line, Lec-2 and Lec-8, were used in these experiments. Lec-2 cells are deficient in cytidine monophosphate-sialic acid Golgi transporter and therefore lack sialic acid residues on their surface glycans, which allows exposure of the most common penultimate saccharide, galactose. Lec-8 cells are deficient in uridine diphosphate-galactose Golgi transporter and are consequently devoid of galactose saccharides on their surface glycan structures. When examining vector binding to these CHO cell lines, the expected results were observed for AAV9. A low level of binding was observed on Pro-5 cells, but was shown to increase 100-fold on Lec-2 cells, which have terminal galactose residues free for AAV9 binding. Binding to Lec-8 cells was decreased back to baseline level due to their lack of cell-surface galactose. Thirteen out of fourteen of the mutant vectors demonstrated this trend of increased binding on Lec-2 cells, suggesting they retained the ability to bind galactose. However, mutation of the asparagine residue at position 470 to alanine (N470A) reduced binding to Lec-2 cells to the level observed on Pro-5 and Lec-8 cells. This indicated that N470 is required for AAV9 binding to galactose.

2. Additional Amino Acids Located in Close Proximity to N470 are Required for AAV9 Galactose Binding Additional AAV9 mutants were generated to determine whether any of the amino acids structurally surrounding N470 are also contributing to galactose binding. This second set of mutants targeted amino acids throughout multiple defined variable regions (VRs) of the capsid, including VR I, IV, V, and VII, which in the assembled icosahedral structure of the virion come into close contact with each other. Nineteen amino acids near N470 were selected for mutation to alanine (FIG. 3B) and vectors were produced by small-scale methods. As before, all of the mutants yielded high titer vector similar to the AAV9 control, suggesting none of the mutations had a negative effect on capsid assembly. The mutant vectors were then tested for their ability to bind Pro-5, Lec-2, and Lec-8 cells (FIG. 3B). Again, AAV9 showed the expected result of a 100-fold increase in binding to Lec-2 cells compared to Pro-5 and Lec-8 cells. While most of the mutants tested also exhibited this phenotype, four mutants demonstrated a loss of binding to Lec-2 cells. Mutation of D271, N272, Y446, or W503 all abolished the ability of AAV9 to bind galactose.

Alongside these nineteen alanine mutants, four other AAV9 site-directed mutations were performed. The non-polar amino acids A472 and V473 are located directly next to N470 and could potentially play a role in galactose binding. To test this idea, A472 and V473 were both mutated to either the polar amino acid serine or the charged amino acid aspartic acid. Construction of these vectors by small-scale methods was successful and titers were achieved similar to wild type AAV9. When examining the binding of these vectors to CHO cells, it was observed that all four of these mutants (A472S, A472D, V473S, and V473D) lost the ability to bind Lec-2 cells. This suggests that these non-polar residues are essential to the formation of the galactose binding region because adding either polarity or charge to this region disrupted interaction with galactose.

3. Galactose Binding of AAV9 Mutants is Indicative of in Vitro Transduction Efficiency To assess the transduction of AAV9 mutants in vitro, vectors expressing firefly luciferase (ffLuc) were added to Pro-5 and Lec-2 cells. The five mutants that lost galactose binding (N470A, D271A, N272A, Y446A, and W503A), as well as two mutants that retained galactose binding (S469A and E500A) and an AAV9 control vector were added to the cells (MOI=104) and evaluated for ffLuc expression 48 hours later. As expected, the mutants that lack galactose binding ability demonstrated a 3-fold or greater decrease in transduction of Lec-2 cells compared to AAV9, S469A, and E500A. W503A and N272A showed the lowest transduction levels, just above background. On Pro-5 cells, the overall transduction was 2- to 5-fold lower because these cells lack abundant terminal galactose residues for binding. However, a similar trend in transduction was still observed as that determined for Lec-2 cells. The mutants deficient in galactose binding showed the lowest transduction and the two mutants that retained galactose binding (S469A and E500A), as well as the AAV9 control vector, demonstrated higher levels of transduction. E500A, however, showed approximately 2-fold higher expression than AAV9 on Pro-5 cells, suggesting that this vector may have favorable intracellular interactions.

4. Mutant Vectors Deficient in Galactose Binding do not Transduce Conducting Airway Epithelium Delivering neuraminidase (NA) intranasally to mice prior to intranasal administration of AAV9 vector allows efficient AAV9 transduction of conducting airway epithelium of the lung. This occurs because NA cleaves terminal sialic acid residues from the surface glycans of the airway cells, which exposes the underlying galactose residues and allows AAV9 binding and transduction. Whether the mutant vectors that are deficient in galactose binding can transduce conducting airway epithelium in vivo was studied. Vectors ($10^{11}$ GC) expressing nuclear-targeted LacZ (nLacZ) were delivered intranasally to mice one hour post instillation of 100 mU NA and then twenty-one days later lungs were removed and stained for β-gal expression. The AAV9 control vector demonstrated efficient conducting airway transduction, as expected based on our previous results. The five mutants that lost the ability to bind galactose (N470A, D271A, N272A, Y446A, and W503A) were unable to transduce conducting airway epithelium, further demonstrating their inability to bind galactose in vivo. The S469A and E500A mutants, which retained galactose binding, displayed efficient conducting airway transduction similar to AAV9.

5. The Amino Acids Necessary for Binding Form a Pocket on the AAV9 Capsid that Supports Interaction with Galactose Using knowledge of the structure of AAV9, the location of the amino acids important for galactose binding on the surface of the capsid was determined. A molecular docking approach was utilized to identify the galactose binding sites on an AAV9 VP trimer. The top 100 docking results were evaluated and docking solutions that placed galactose on the inner surface of the capsid were discarded. The remaining 13 solutions all dock galactose in close contact with N470, with 12 out of 13 solutions docking galactose in between N470 and W503. N470, D271, N272, Y446, and W503 form a pocket at the base of the protrusions surrounding the 3-fold axes of symmetry. The pocket is formed by the outside surface of the protrusions facing the 2- and 5-fold axes and a small surface protrusion between the 2- and 5-fold axes formed by VR I. AAV9 contains a binding pocket where it is further illustrated how the galactose residue fits into this region. The non-polar A472 and V473 amino acids found to be important for galactose binding are located at the base of the binding pocket and therefore likely allow successful insertion of the galactose saccharide. An interesting feature of the galactose binding site is that the amino acids that have been shown to be important for binding are from two different monomers, where Y446, N470, A472, and V473 make up the floor of the binding pocket, and the amino acids that make up the roof of the binding pocket, D271, N272, and W503, are from another contributing monomer. This may provide a mechanism to ensure that only properly assembled capsids can bind to the receptor. Significantly, following identification of the galactose binding pocket, an attempt to dock a sialic acid molecule into the same capsid region showed that this glycan cannot be accommodated in the pocket due to steric hindrance. This observation is consistent with the lack of sialic acid binding by AAV9.

C. Discussion

Previous experiments studying the cell surface glycan interactions of AAV9 demonstrated that this vector uses galactose as a cellular receptor. Analysis of AAV9 binding and transduction of multiple cell lines, including Pro-5, HEK293, and Huh-7 cells, revealed that the enzymatic removal of terminal sialic acid residues from cell surface glycans using NA led to a significant increase in AAV9 binding. This increase was due to the exposure of the underlying galactose saccharides, which facilitated AAV9 binding and transduction. Further studies using the CHO glycosylation mutant cell lines Lec-2 and Lec-8, as well as lectin competition assays, confirmed this role of galactose. Additionally, NA delivered intranasally to mice led to an increase in terminal galactose residues on the surface of airway cells and therefore an increase in AAV9 transduction.

The goal of this study was to identify the amino acids of the AAV9 capsid required for galactose binding, which we determined to include N470, D271, N272, Y446, and W503. Comparing the galactose binding site of AAV9 to that of other galactose binding proteins, similarities were discovered in regard to amino acid composition. The interaction of sugars with aromatic residues is common in the binding site of carbohydrate-binding proteins and has been observed for galactose-specific proteins (Elgavish, et al., 1997, *Trends Biochem Sci* 22(12): 462-7.; Sujatha, et al., 2005, *Biochemistry* 44(23): 8554-62). These residues form hydrophobic interactions with the saccharide and are also involved in the discrimination of galactose from other sugars, such as glucose (Elgavish, 1997; Sujatha, 2005). This is consistent with our mapped binding site for AAV9, which contains two aromatic residues, Y446 and W503. Additionally, many galactose binding proteins contain polar and charged amino acids, including asparagine, aspartic acid, and glutamine, that have been shown to contribute to galactose binding by forming hydrogen bonds with the hydroxyl groups of the sugar (Montfort, et al., 1987, *J Biol Chem* 262(11): 5398-403; Elgavish, 1997). It is likely that N470, D271, and N272 of the AAV9 capsid are forming similar interactions with galactose. The location of the receptor binding domain of other AAV serotypes has also been determined. The HS binding site of AAV2 was mapped to five amino acids: R484, R487, R585, R588 and K532 (Kern, 2003 *J Virol* 77(20): 11072-81.; Opie, 2003, *J Virol* 77(12): 6995-7006). These amino acids form a basic patch on the inside of each 3-fold symmetry-related protrusion of the capsid. AAV6, which has also been shown to bind to HS, contains a similar basic stretch of amino acids in analogous positions as observed for AAV2, including R485, R488, K528, and K533 (Ng, et al., 2010, *J Virol* 84(24): 12945-57). In addition, through mutagenesis studies, K493, K459, R576, and K531, have all been shown to be necessary for AAV6 HS binding and are located in neighboring positions. The galactose binding domain of AAV9, located at the base of the protrusions surrounding the 3-fold axes, is on the opposite side of this structure compared to the AAV2 HS binding region, which is located on the inside surface facing the 3-fold axis. The AAV6 HS binding residues are also located on the outside wall of the protrusions, but on the opposite wall closer to VR III and the icosahedral 2-fold axis compared to the AAV9 galactose binding residues. These observations further illustrate the importance of the amino acids and structures that assemble the protrusions surrounding the 3-fold axes and the residues adjacent to this region in receptor recognition for different AAV serotypes. It also supports a proposal that the common structural variability of the AAV capsids, particularly the surface exposed protrusions, have evolved to enable the utilization of different surface molecules for successful infection, which is an important determinant of their respective transduction phenotypes.

AAV9 shows unique characteristics that could potentially be explained by receptor interactions. For example, after intravenous injection, AAV9 can surpass the blood-brain barrier and transduce motor neurons in the spinal cord of adult and neonatal mice and cats, as well as neurons in the neonatal mouse brain and astrocytes in the adult mouse brain. Also, when tested in nonhuman primates, AAV9 transduced motor neurons in the spinal cord and primarily glial cells in the brain. By fluorescent lectin staining, we have previously observed abundant galactose expression on the surface of blood vessels in the mouse brain. AAV9 could possibly be using galactose to facilitate transcytosis across the vasculature, allowing entry into the central nervous system. Engineering the galactose binding domain onto the capsid of other AAV serotypes may allow the transfer of AAV9's attractive phenotypes and the development of novel vectors for gene therapy.

Example 6—NA Pre-Treatment Improves AAV-Mediated ffLuc Expression in Mouse Nasal Airway C57BL6 mice (6-8 weeks of age, 20-25 g of weight, male) were anaesthetized with a mixture of ketamine/xylazine. Mice were then given 582 μl of neuraminidase (NA) from Vibrio cholera (Sigma, N7885) in each nostril (total of 80-100 mU of NA). Within 10 mins of NA pre-treatment, AAV9 vector ($10^{11}$ GC total dose) expressing firefly luciferase (ffLuc) under the transcriptional control of the chicken β-actin promoter was instilled as two 15 μl aliquots diluted in PBS (15 μl per nare). Mice were allowed to recover and transgene expression (ffLuc) was monitored as early as 24 hrs post vector inoculation.

At the time of luminescence imaging mice were anaesthetized and given luciferin [15 μl of a 15 mg/ml D-Luciferin solution (Caliper Life Sciences, Hopkinton, Mass.) per nare in both nares] and imaged for expression within 5 mins of luciferin application. Mice were allowed to recover for subsequent imaging procedures at days 3, 7, 14, 21 and 28.

These results are illustrated in the bar chart of FIG. 5. These data show an approximately 2 fold improvement in firefly luciferase gene expression in the nasal airway following pre-treatment with neuraminidase. This difference was observed on two separate occasions. Also, addition of neuraminidase resulted in a rapid onset of gene expression with the highest gene expression observed within 24 hours of AAV9 vector installation that waned to steady state levels within a week.

All publications, patent documents, and GenBank sequences cited in this specification are incorporated herein by reference. While the invention has been described with reference to particularly preferred embodiments, it will be appreciated that modifications can be made without departing from the spirit of the invention.

The invention claimed is:

1. A recombinant adeno-associated virus (AAV) 9 (AAV9) viral particle modified to substantially decrease or ablate the native ability of wild-type (wt) AAV9 to transduce conducting airway, said viral particle having an AAV9 capsid protein which comprises AAV vp1 proteins, AAV vp2 proteins, and AAV vp3 proteins, wherein the AAV vp1 proteins have an amino acid sequence having at least 95% identity to the full length of the amino acids 1 to 736 of SEQ ID NO:1, and in which a native AAV9 amino acid selected from the group consisting of position 271, 446, or 470 based on the positions of SEQ ID NO:1 when aligned along the full length of the amino acids 1 to 736 of SEQ ID NO:1, is substituted by another amino acid.

2. The recombinant AAV viral particle according to claim 1, wherein the substituted amino acid has a small, uncharged side chain.

3. The recombinant AAV viral particle according to claim 2, wherein the substituted amino acid has a small side chain with a methyl group.

4. The recombinant AAV viral particle according to claim 2, wherein the substituted amino acid is selected from Valine (Val), Isoleucine (Ile), or Leucine (Leu).

5. The recombinant AAV viral particle according to claim 1, wherein the substituted amino acid is selected from Arginine (Arg), Histidine (His), Lysine (Lys), Aspartic Acid (Asp), Glutamic Acid (Glu), Serine (Ser), Threonine (Thr), Glutamine (Gln), Cysteine (Cys), Methionine (Met), Phenylalanine (Phe), Tyrosine (Tyr), or Tryptophan (Trp).

6. The recombinant AAV viral particle according to claim 1, wherein the substituted amino acid is not a Proline (Pro).

7. The recombinant AAV viral particle according to claim 1, wherein the substituted amino acid is an Alanine (Ala).

8. The recombinant AAV viral particle according to claim 1, wherein the modified AAV9 viral particle retains liver and heart transduction similar to the wt AAV9.

9. The recombinant AAV viral particle according to claim 1, wherein the modified AAV9 viral particle has a capsid protein which is at least 95% identical to vp3 protein of the wt AAV9.

10. The recombinant AAV viral particle according to claim 9, wherein the wt AAV9 vp3 protein has an amino acid sequence of amino acids 203 to 736 of SEQ ID NO: 1.

11. The recombinant AAV viral particle according to claim 1, further comprising a minigene packaged in the capsid, wherein the minigene comprises a 5' AAV inverted terminal repeat (ITR), a transgene, regulatory sequences which drives expression of the transgene, and a 3' ITR.

12. A method of generating a recombinant AAV viral particle according to claim 1, comprising culturing a host cell which contains a nucleic acid sequence encoding the AAV capsid protein; a functional rep gene; a minigene comprising a 5' AAV inverted terminal repeat (ITR), a transgene, regulatory sequences which drives expression of the transgene, and a 3' ITR; and sufficient helper functions to permit packaging of the minigene into the AAV capsid.

13. A composition comprising a recombinant AAV viral particle according to claim 1 and a pharmaceutically acceptable carrier.

14. A method for treating a disorder, comprising administering a recombinant AAV viral particle according to claim 1.

* * * * *

SEQUENCE LISTING

```
<160> NUMBER OF SEQ ID NOS: 4

<210> SEQ ID NO 1
<211> LENGTH: 736
<212> TYPE: PRT
<213> ORGANISM: Unknown
<220> FEATURE:
<223> OTHER INFORMATION: capsid of hu.14/AAV9

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285
```

```
Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Phe Pro
        355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
```

```
                705               710               715               720
        Tyr Ser Glu Pro Arg Pro Ile Gly Thr Arg Tyr Leu Thr Arg Asn Leu
                        725               730               735

<210> SEQ ID NO 2
<211> LENGTH: 25
<212> TYPE: DNA
<213> ORGANISM: Artificial Sequence
<220> FEATURE:
<223> OTHER INFORMATION: F primer based on homo sapiens

<400> SEQUENCE: 2
agcaatagca tcacaaattt cacaa                                           25

<210> SEQ ID NO 3
<211> LENGTH: 29
<212> TYPE: DNA
<213> ORGANISM: Artificial Sequence
<220> FEATURE:
<223> OTHER INFORMATION: R primer based on homo sapiens

<400> SEQUENCE: 3
ccagacatga taagatacat tgatgagtt                                       29

<210> SEQ ID NO 4
<211> LENGTH: 36
<212> TYPE: DNA
<213> ORGANISM: Artificial Sequence
<220> FEATURE:
<223> OTHER INFORMATION: TaqMan probe based on homo sapiens

<400> SEQUENCE: 4
agcatttttt tcactgcatt ctagttgtgg tttgtc                               36
```

UNITED STATES PATENT AND TRADEMARK OFFICE
CERTIFICATE OF CORRECTION

| | |
|---|---|
| PATENT NO. | : 11,766,448 B2 |
| APPLICATION NO. | : 17/159735 |
| DATED | : September 26, 2023 |
| INVENTOR(S) | : James M. Wilson, Christie L. Bell and Luc H. Vandenberghe |

It is certified that error appears in the above-identified patent and that said Letters Patent is hereby corrected as shown below:

In the Specification

In Column 1, the paragraph immediately following the heading "STATEMENT REGARDING FEDERALLY SPONSORED RESEARCH OR DEVELOPMENT" is replaced with the following paragraph:
-- This invention was made with government support under HL059407 awarded by the National Institutes of Health. The government has certain rights in the invention. --

Signed and Sealed this
Twenty-third Day of January, 2024

Katherine Kelly Vidal
*Director of the United States Patent and Trademark Office*